(12) United States Patent
Hafner et al.

(10) Patent No.: US 7,358,047 B2
(45) Date of Patent: Apr. 15, 2008

(54) METHODS OF FORMING CIRCULAR NUCLEIC ACID PROBES AND USES THEREOF

(75) Inventors: Gregory John Hafner, Manly West (AU); Philip Morrison Giffard, Balmoral (AU); Lindsay Colin Wolter, Holland Park (AU); James Langham Dale, Moggill (AU); Mark Richard Stafford, Herston (AU); Ilin Chen Hai-Ni Yang, Mount Gravatt East (AU); Joanne Voisey, Enoggera (AU)

(73) Assignee: QIAGEN GmbH, Hilden (DE)

( * ) Notice: Subject to any disclaimer, the term of this patent is extended or adjusted under 35 U.S.C. 154(b) by 420 days.

(21) Appl. No.: 10/917,580

(22) Filed: Aug. 13, 2004

(65) Prior Publication Data

US 2005/0079523 A1 Apr. 14, 2005

Related U.S. Application Data

(63) Continuation of application No. 09/460,078, filed on Dec. 14, 1999, now Pat. No. 6,830,884.

(60) Provisional application No. 60/112,370, filed on Dec. 15, 1998.

(51) Int. Cl.
*C12Q 1/68* (2006.01)
*C12P 19/34* (2006.01)
*C07H 21/04* (2006.01)

(52) U.S. Cl. .................. 435/6; 435/91.1; 435/91.2; 536/23.1; 536/24.3

(58) Field of Classification Search .............. None
See application file for complete search history.

(56) References Cited

U.S. PATENT DOCUMENTS

| 5,591,609 A | 1/1997 | Auerbach |
| 5,648,245 A | 7/1997 | Fire et al. |
| 5,714,320 A | 2/1998 | Kool |
| 5,854,033 A | 12/1998 | Lizardi |
| 5,876,924 A | 3/1999 | Zhang et al. |
| 5,942,391 A | 8/1999 | Zhang et al. .................. 435/6 |
| 6,143,495 A | 11/2000 | Lizardi et al. |

(Continued)

FOREIGN PATENT DOCUMENTS

JP 4-304900 10/1992

(Continued)

OTHER PUBLICATIONS

Non-Final Rejection mailed May 19, 2003 in re: U.S. Patent No. 6,830,884.

(Continued)

*Primary Examiner*—Kenneth R. Horlick
*Assistant Examiner*—Mark Staples
(74) *Attorney, Agent, or Firm*—Needle & Rosenberg, P.C.

(57) ABSTRACT

The present invention relates generally to a method of amplifying closed circular nucleic acid probes and, more particularly, to a method of amplifying closed circular nucleic acid probes by rolling circle amplification. The method of the present invention is useful in a range of applications involving the detection of nucleic acid sequences such as, but not limited to, the identification of genetic disorders, genetic variants or the presence of microbiological or viral agents.

6 Claims, 26 Drawing Sheets

U.S. PATENT DOCUMENTS

| | | | |
|---|---|---|---|
| 6,183,960 | B1 | 2/2001 | Lizardi |
| 6,203,984 | B1 | 3/2001 | Hu et al. |
| 6,210,884 | B1 | 4/2001 | Lizardi |
| 6,316,229 | B1 | 11/2001 | Lizardi et al. ............. 435/91.1 |
| 6,329,150 | B1 | 12/2001 | Lizardi et al. |
| 6,344,329 | B1 | 2/2002 | Lizardi |
| 6,830,884 | B1 * | 12/2004 | Hafner et al. .................. 435/6 |
| 2002/0136180 | A1 | 9/2002 | Lizardi |
| 2003/0032024 | A1 | 2/2003 | Lizardi |
| 2003/0059786 | A1 | 3/2003 | Ward et al. |

FOREIGN PATENT DOCUMENTS

| | | |
|---|---|---|
| JP | 5-146299 | 6/1993 |
| WO | WO 92/01813 | 2/1992 |
| WO | WO 96/33207 | 10/1996 |
| WO | WO 97/19193 | 5/1997 |
| WO | WO 97/42346 | 11/1997 |
| WO | WO 98/04746 | 2/1998 |

OTHER PUBLICATIONS

Amendment and Response filed Nov. 24, 2003 in re: U.S. Patent No. 6,830,884.

Final Rejection mailed Feb. 13, 2004 in re: U.S. Patent No. 6,830,884.

Amendment and Response filed Jun. 17, 2004 in re: U.S. Patent No. 6,830,884.

Loakes et al. "5-Nitroindole as a universal base analogue" Nucleic Acids Res. 1994, 22(20):45039-4043.

Liu, D., et al. (1995) "Rolling circle DNA synthesis: small circular oligonucleotides as efficient templates for DNA polymerases" *J. Am. Chem. Soc. 118*: 1587-1594.

Fire, A., et al. (1995) "Rolling replication of short DNA circles" *Proc. Natl. Acad. Sci. USA 92*: 4641-4645.

Guatelli, J.C., et al. (1990) "Isothermal, in vitro amplification of nucleic acids by a multienzyme reaction molded after retroviral replication" *Proc. Natl. Acad. Sci. USA 87*:1874-1878.

Kwoh, D.Y., et al. (1989) "Transcription-based amplification system and detection of amplified human immunodeficiency virus type 1 with a bead-based sandwich hybridization format" *Proc. Natl. Acad. Sci. USA 86*: 1173-1177.

Landergren, U., et al. (1988) "A Ligase-Mediated Gene Detection Technique" *Science 241*: 1077-1080.

Lizardi, P.M., et al. (1998) "Mutation detection and single-molecule counting using isothermal rolling-circle amplification" *Nature Genetics 19*: 225-232.

Lizardi, P.M., et al. (1997) "Fish with a twist" *Nature Genetics 16*: 217-218.

Nilsson, M., et al. (1994) "Padlock Probes: Circularizing Oligonucleotides for Localized DNA Detection" *Science 265*: 2085-2088.

Nilsson, M., et al. (1997) "Padlock probes reveal single-nucleotide differences, parent or origin and in situ distribution of centromeric sequences in human chromosomes 13 and 21" *Nature Genetics 16*: 252-255.

Saiki, R.K., et al. (1985) "Enzymatic Amplifications of bata-Globin Genomic Sequences and Restriction Site Analysis for Diagnosis of Sickle Cell Anemia" *Science 230*: 1350-1354.

Tyagi, S., et al. (1996) "Extremely sensitive, background-free gene detection using binary probes and Q replicase" *Proc. Natl. Acad. Sci. USA 93*: 5395-5400.

Wang, S., et al. (1994) "Circular RNA oligonucleotides. Synthesis, nucleic acid binding properties, and a comparison with circular DNAs" *Nucleic Acids Research 22*(12): 2326-2333.

Zhang, D.Y., et al. (1998) "Amplification of target-specific, ligation-dependent circular probe" *Gene 211*: 277-285.

* cited by examiner

Padlock FV2 - Schematic

Oligonucleotide Design for Factor V Gene Detection Using RCA

```
Padlock                     | Target Binding Region |                        | Target Binding Region |
Padlock FV2:         5' AGGAATACAGGTATTTTGTCCTTGCGCGGTGAGCTATATGGGACTATGAATTCTAATAGGACTACTTCTAATCTGTAAGAG 3'   83mer
Spacers
LigW :               5' p-CAGATCCC(biotin-dT)GGACAGGCG 3'                                                       18mer Targets
Wildtype Target:     5' TACTTCAAGGACAAAATACCTGTATTCCTCGCCTGTCCAGGGATCTGCTCTTACAGATTAGAAGTAGTCCTATT 3'          74mer Spacer
Amplification Primers
FVComT:              5' p-TTTTTTTTTTTGTCCCCATATAGCTCACCG                                                        29mer
FVW1:                5' Flu- CAGATCCCTGGACAGACG                                                                 18mer
```

Figure 4 (i)

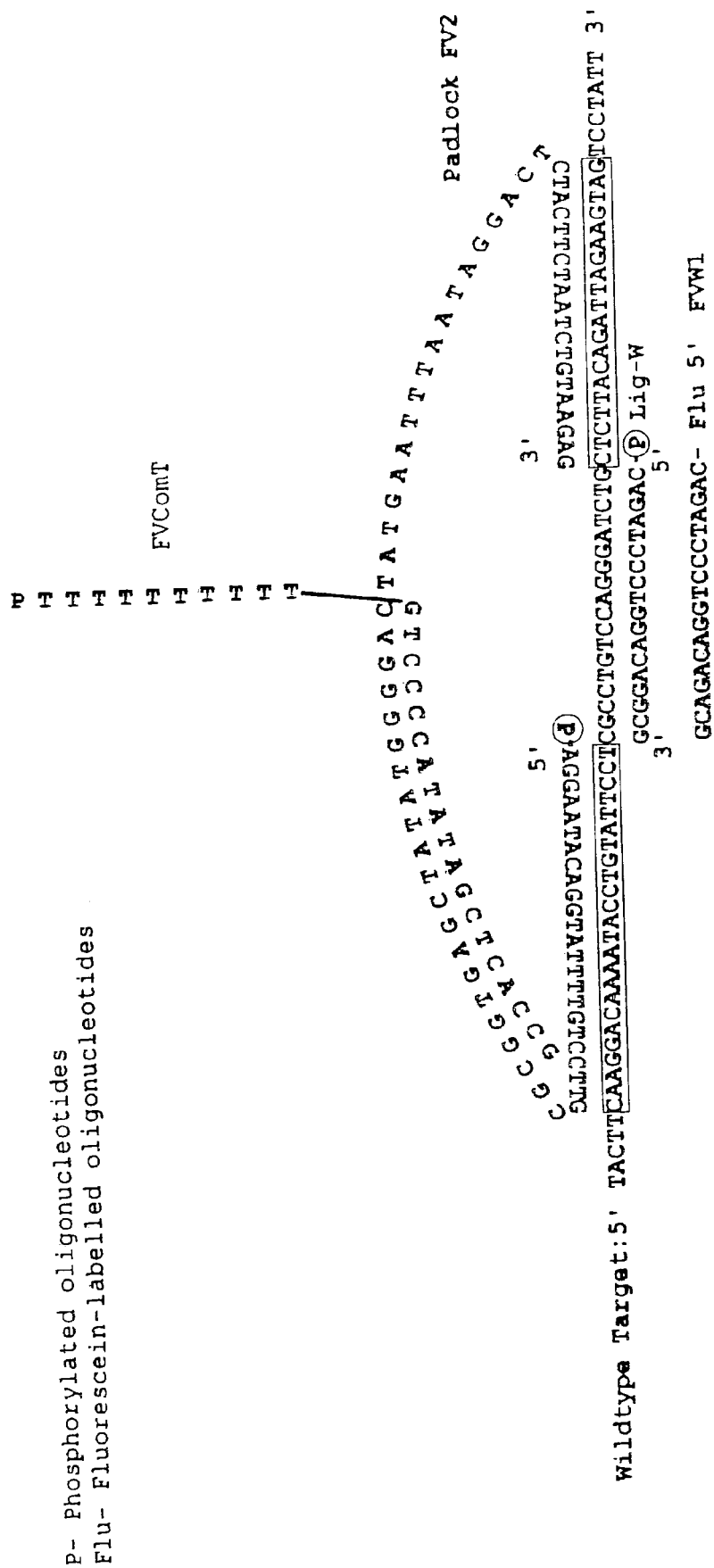
Figure 4 (ii)

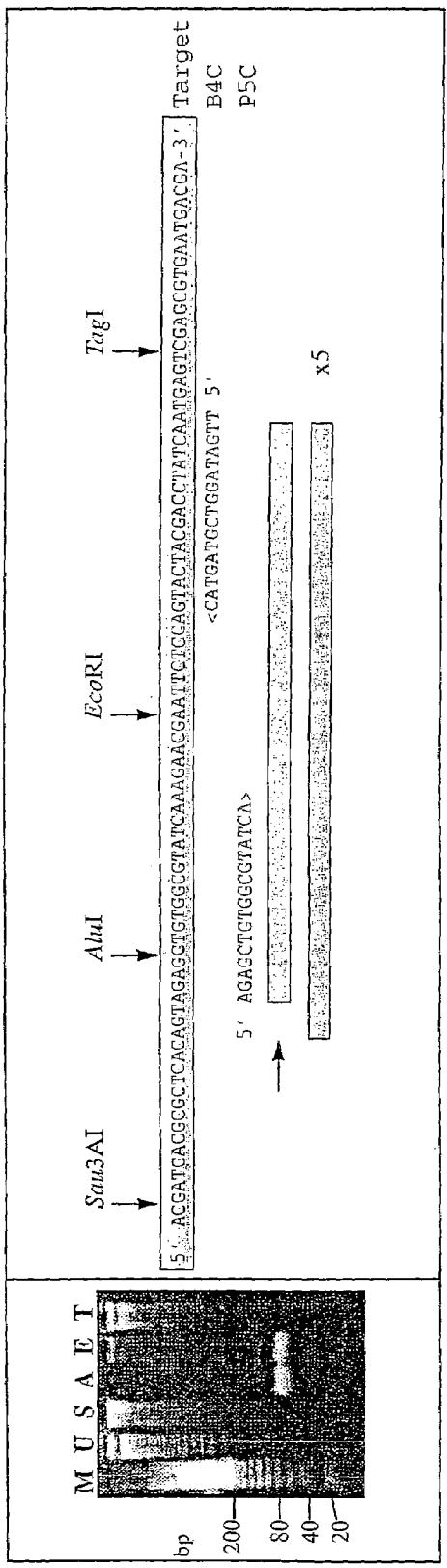
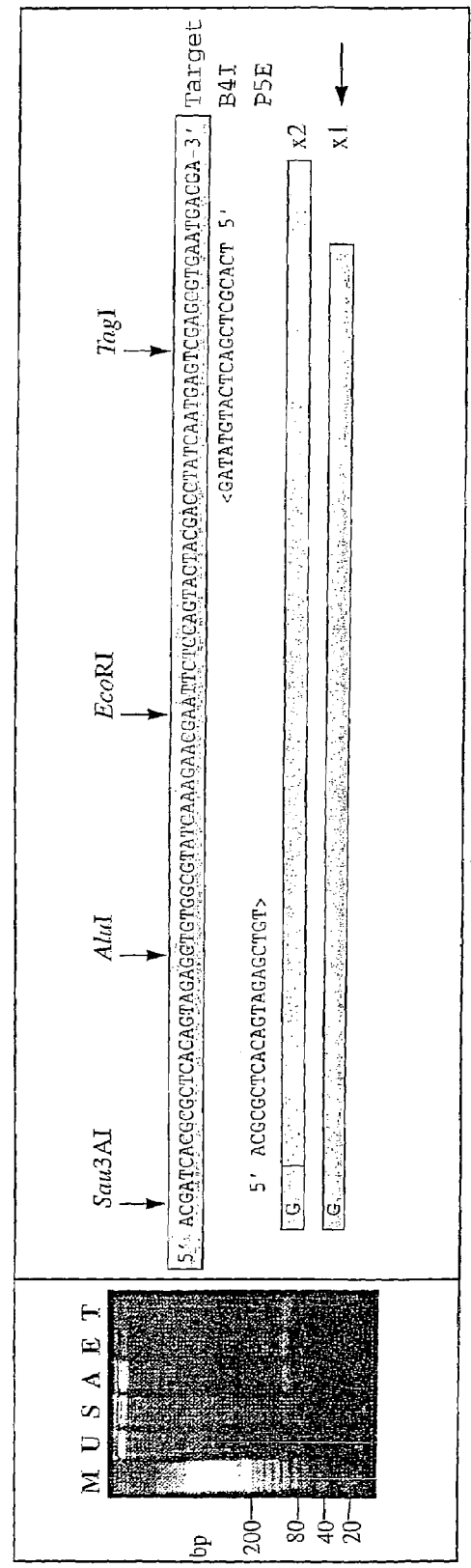
Figure 6a
Figure 6b

Template Concentration (pmol)

$10^0\ 10^{-1}\ 10^{-2}\ 10^{-3}\ 10^{-4}\ 10^{-5}\ 0$

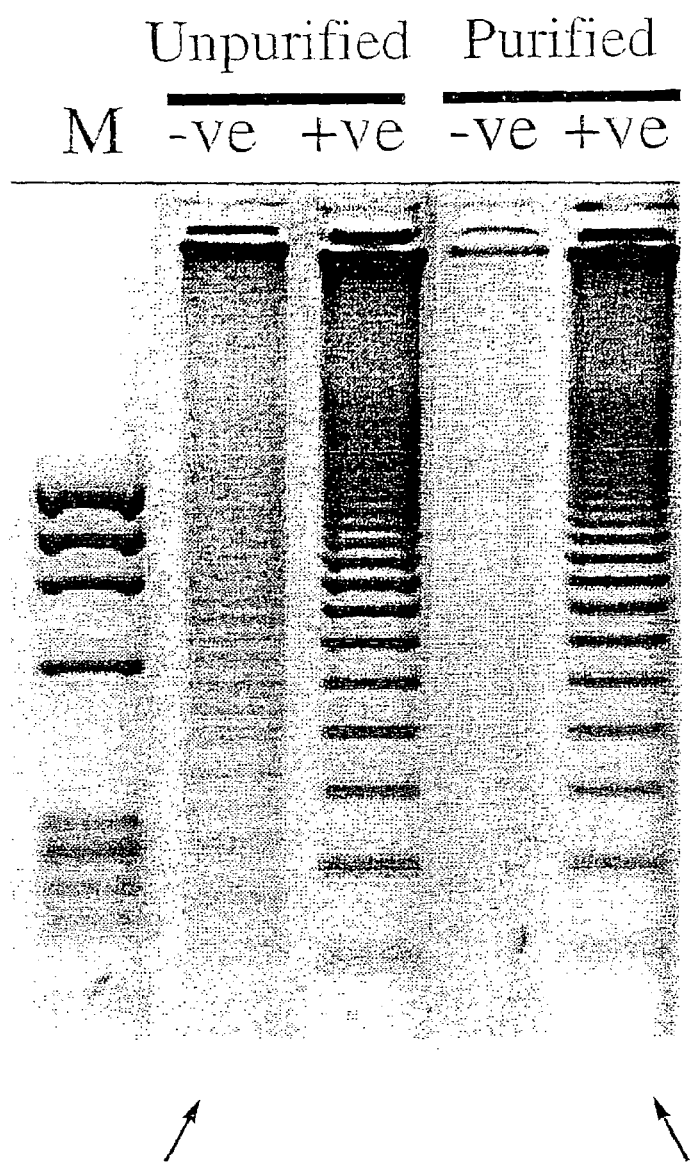
Amp X
(Negative
RCA control)
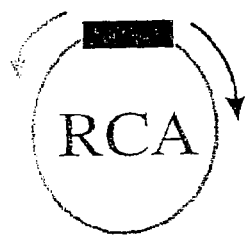
Figure 10

Oligonucleotide Design for Factor V Gene Detection Using RCA

```
Padlock                   | 3' Binding Region        |         Eco RI      |            5' Binding Region             |
Padlock FV2:           5' AGGAATACAGGTATTTGTCCTTGCGCGGTGAGCTATATGGGACTATGAATTTCTAATAGGACTACTTCTAATCTGTAAGAG 3'
(83mer)
Spacers
LigW :                 5' p-CAGATCCC(biotin-dT)GGACAGGCG 3'                                                            18mer
LigM :                 5' p-CAGATCCC(biotin-dT)GGACAGGCA 3'                                                            18mer
Targets
Wildtype Target:       5' TACTTCAAGGACAAAATACCTGTATTCCTGCCTGTCCTGGATCTGCTCTTACAGATTAGAAGTAGTCCTATT 3'                 74mer
Mutant Target:         5' TACTTCAAGGACAAAATACCTGTATTCCTGCCTGTCCTGGGATCTGCTCTTACAGATTAGAAGTAGTCCTATT 3'                74mer Amplification Primers
PadFV3:                5' GAAATTCATAGTCCCC                                                                             16mer
PadFV4:                5' CGCGGTGAGCTATAT                                                                              15mer
```

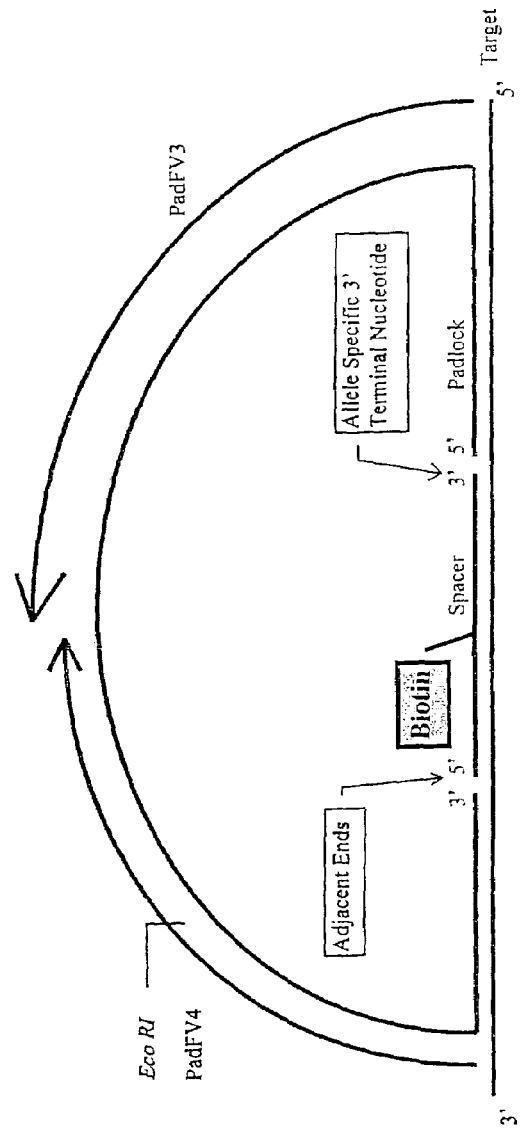

Figure 11

Lane 1: MW markers
Lane 2: No target, *C. pneumoniae* specific primer
Lane 3: *C. pneumoniae* target, *C. pneumoniae* specific primer, no ligase
Lane 4: *C. pneumoniae* target, *C. pneumoniae* specific primer
Lane 5: *C. pneumoniae* target, *C. trachomatis* specific primer
Lane 6: *C. trachomatis* target, *C. trachomatis* specific primer
Lane 7: *C. trachomatis* target, *C. pneumoniae* specific primer Lane 1: MW markers
Lane 2: No target, 10 pmoles FVComT
Lane 3: 0 pmoles FVComT
Lane 4: 0.1 pmole FVComT
Lane 5: 1 pmole FVComT
Lane 6: 5 pmoles FVComT
Lane 7: 10 pmoles FVComT

SEQUENCE LISTING

<160> NUMBER OF SEQ ID NOS: 31

<210> SEQ ID NO 1
<211> LENGTH: 90
<212> TYPE: DNA
<213> ORGANISM: Primer

<400> SEQUENCE: 1
acgatcacgc gctcacagta gagctgtggc gtatcaaaga acgaattctc cagtactacg    60
acctatcaat gagtcgagcg tgaatgacga    90

<210> SEQ ID NO 2
<211> LENGTH: 17
<212> TYPE: DNA
<213> ORGANISM: Primer

<400> SEQUENCE: 2
agagctgtgg cgtatca    17

<210> SEQ ID NO 3
<211> LENGTH: 22
<212> TYPE: DNA
<213> ORGANISM: Primer

<400> SEQUENCE: 3
tagtgctgtg gcgtatcaaa ga    22

<210> SEQ ID NO 4
<211> LENGTH: 21
<212> TYPE: DNA
<213> ORGANISM: Primer

<400> SEQUENCE: 4
acgcgctcac agtagagctg t    21

<210> SEQ ID NO 5
<211> LENGTH: 18
<212> TYPE: DNA
<213> ORGANISM: Primer

<400> SEQUENCE: 5
acgatcacgc gctcacag    18

<210> SEQ ID NO 6
<211> LENGTH: 17
<212> TYPE: DNA
<213> ORGANISM: Primer

<400> SEQUENCE: 6
catgatgctg gatagtt    17

<210> SEQ ID NO 7
<211> LENGTH: 24
<212> TYPE: DNA
<213> ORGANISM: Primer

```
<400> SEQUENCE: 7
aggtcatgat gctggatagt tact                                        24

<210> SEQ ID NO 8
<211> LENGTH: 21
<212> TYPE: DNA
<213> ORGANISM: Primer

<400> SEQUENCE: 8
gatagttact cagctcgcac t                                           21

<210> SEQ ID NO 9
<211> LENGTH: 120
<212> TYPE: DNA
<213> ORGANISM: Escherichia coli

<400> SEQUENCE: 9
atgacgagcg taatggctgg cctgttgaac aagtctggaa agaaatgcat aagcttttgc    60
cattctcacc ggattcagtc gtcactcatg gtgatttctc acttgataac cttattttg   120

<210> SEQ ID NO 10
<211> LENGTH: 25
<212> TYPE: DNA
<213> ORGANISM: Primer

<400> SEQUENCE: 10
atgacgagcg taatggctgg cctgt                                       25

<210> SEQ ID NO 11
<211> LENGTH: 27
<212> TYPE: DNA
<213> ORGANISM: Primer

<400> SEQUENCE: 11
tgcataagct tttgccattc tcaccgg                                     27

<210> SEQ ID NO 12
<211> LENGTH: 25
<212> TYPE: DNA
<213> ORGANISM: Primer

<400> SEQUENCE: 12
aagagtgaac tattggaata aaaac                                       25

<210> SEQ ID NO 13
<211> LENGTH: 83
<212> TYPE: DNA
<213> ORGANISM: Probe

<400> SEQUENCE: 13
aggaatacag gtattttgtc cttgcgcggt gagctatatg gggactatga atttctaata    60
ggactacttc taatctgtaa gag                                         83

<210> SEQ ID NO 14
<211> LENGTH: 17
<212> TYPE: DNA
<213> ORGANISM: Probe

<400> SEQUENCE: 14
cagatcccgg acaggcg                                                17
```

```
<210> SEQ ID NO 15
<211> LENGTH: 17
<212> TYPE: DNA
<213> ORGANISM: Probe

<400> SEQUENCE: 15
cagatcccgg acaggca                                                    17

<210> SEQ ID NO 16
<211> LENGTH: 74
<212> TYPE: DNA
<213> ORGANISM: mammalian

<400> SEQUENCE: 16
tacttcaagg acaaaatacc tgtattcctc gcctgtccag ggatctgctc ttacagatta     60
gaagtagtcc tatt                                                       74

<210> SEQ ID NO 17
<211> LENGTH: 74
<212> TYPE: DNA
<213> ORGANISM: mammalian

<400> SEQUENCE: 17
tacttcaagg acaaaatacc tgtattcctt gcctgtccag ggatctgctc ttacagatta     60
gaagtagtcc tatt                                                       74

<210> SEQ ID NO 18
<211> LENGTH: 16
<212> TYPE: DNA
<213> ORGANISM: Primer

<400> SEQUENCE: 18
gaaattcata gtcccc                                                     16

<210> SEQ ID NO 19
<211> LENGTH: 15
<212> TYPE: DNA
<213> ORGANISM: Primer

<400> SEQUENCE: 19
cgcggtgagc tatat                                                      15

<210> SEQ ID NO 20
<211> LENGTH: 71
<212> TYPE: DNA
<213> ORGANISM: mammalian

<400> SEQUENCE: 20
ctaataggac tacttctaat ctgtaagagc agatccctgg acaggcgagg aatacaggta     60
ttttgtcctt g                                                          71

<210> SEQ ID NO 21
<211> LENGTH: 71
<212> TYPE: DNA
<213> ORGANISM: mammalian

<400> SEQUENCE: 21
ctaataggac tacttctaat ctgtaagagc agatccctgg acaggcaagg aatacaggta     60
ttttgtcctt g                                                          71

<210> SEQ ID NO 22
```

```
<211> LENGTH: 16
<212> TYPE: DNA
<213> ORGANISM: Primer

<400> SEQUENCE: 22
gatccctgga cagacg                                              16

<210> SEQ ID NO 23
<211> LENGTH: 16
<212> TYPE: DNA
<213> ORGANISM: Primer

<400> SEQUENCE: 23
gatccctgga cagaca                                              16

<210> SEQ ID NO 24
<211> LENGTH: 29
<212> TYPE: DNA
<213> ORGANISM: Primer

<400> SEQUENCE: 24
tttttttttt gtcccatat agctcaccg                                 29

<210> SEQ ID NO 25
<211> LENGTH: 18
<212> TYPE: DNA
<213> ORGANISM: Primer

<400> SEQUENCE: 25
cagatccctg gacagacg                                            18

<210> SEQ ID NO 26
<211> LENGTH: 12
<212> TYPE: DNA
<213> ORGANISM: Probe

<400> SEQUENCE: 26
ggatgactca tt                                                  12

<210> SEQ ID NO 27
<211> LENGTH: 52
<212> TYPE: DNA
<213> ORGANISM: Chlamydia

<400> SEQUENCE: 27
tccttaactt tctataatct gcaaactagt attttatttt aggacggcca tg       52

<210> SEQ ID NO 28
<211> LENGTH: 48
<212> TYPE: DNA
<213> ORGANISM: Chlamydia

<400> SEQUENCE: 28
tccttaaatc ttcttcactc tcttagtttt tattgcagaa ctgcgata           48

<210> SEQ ID NO 29
<211> LENGTH: 67
<212> TYPE: DNA
<213> ORGANISM: Chlamydia

<400> SEQUENCE: 29
gcaggtaaag aaggcgccgc ggtgagctat atggggacta tgaatttgct ccattaaagc   60
aaaattgc                                                            67
```

```
<210> SEQ ID NO 30
<211> LENGTH: 21
<212> TYPE: DNA
<213> ORGANISM: Chlamydia

<400> SEQUENCE: 30
ccattaaagc aaattgcaag t                                              21

<210> SEQ ID NO 31
<211> LENGTH: 21
<212> TYPE: DNA
<213> ORGANISM: Chlamydia

<400> SEQUENCE: 31
ccattaaagc aaattgctgc a                                              21
```

METHODS OF FORMING CIRCULAR NUCLEIC ACID PROBES AND USES THEREOF

This application is a continuation of U.S. application Ser. No. 09/460,078 filed on Dec. 14, 1999 (now issued U.S. Pat. No. 6,830,884), which claims benefit of U.S. Provisional Application 60/112,370 filed on Dec. 15, 1998. U.S. application Ser. No. 09/460,078 filed on Dec. 14, 1999 and U.S. Provisional Application 60/112,370 filed on Dec. 15, 1998 are hereby incorporated by reference in their entirety.

FIELD OF THE INVENTION

The present invention relates generally to a method of amplifying closed circular nucleic acid probes and, more particularly, to a method of amplifying closed circular nucleic acid probes by rolling circle amplification. The method of the present invention is useful in a range of applications involving the detection of nucleic acid sequences such as, but not limited to, the identification of genetic disorders, genetic variants or the presence of microbiological or viral agents.

BACKGROUND OF THE INVENTION

Bibliographic details of the publications numerically referred to in this specification are collected at the end of the description.

A variety of nucleic acid amplification technologies exist for the diagnosis of infectious and genetic diseases. Since its invention over a decade ago, the polymerase chain reaction (PCR) (1) has become the method of choice in research and DNA-based diagnostics. This can be attributed to its speed, simplicity and sensitivity. PCR does, however, require temperature cycling, which therefore necessitates the use of expensive thermal cycling equipment. Other amplification techniques, which also require temperature cycling, include the ligase chain reaction (LCR) (2) and the transcription-based amplification system (TAS) (3).

Various other amplification techniques exist which do not require extensive thermal cycling and are essentially isothermal systems. Several of these are transcription-mediated or require RNA as an integral component of the reaction therefore necessitating that the amplification environment is kept free from ribonuclease contamination. These methods include the Qβ replicase system (4), self-sustained sequence replication (3SR) (5) and nucleic acid sequence-based amplification (NASBA) (6).

Presently, there appear to exist at least two isothermal techniques for the amplification of nucleic acid sequences which essentially do not require RNA intermediates. Strand displacement amplification (SDA) (7) is an isothermal technique which relies on the ability of a restriction enzyme to nick a hemiphosphorothioated recognition site and the ability of a polymerase to initiate replication at a nick and displace the downstream strand. The other isothermal technique which can be used to amplify a nucleic acid sequence is rolling circle amplification (RCA).

Various forms of the rolling circle amplification technique have previously been described (8, 9). In essence the technique relies on amplification from a circular DNA probe. The circular probe, commonly referred to as a "padlock probe", is designed such that it has regions at both its 5' and 3' ends which are complementary to the target sequence of interest and are separated by a region of nucleotides of non-target derived origin. Upon hybridisation, the 5' and 3' ends of the probe are brought into close proximity to one another. If the two probe regions are adjacent to one another the 5' and 3' ends can be joined to produce a circular probe. In some instances, however, the probe regions are separated from one another by a small stretch of nucleotides. This region must be filled to achieve the generation of a circular probe. In this regard, a variety of techniques can be utilised including the use of spacer oligonucleotides or by using a DNA polymerase (or a reverse transcriptase in the case of an RNA target) in combination with deoxynucleotide triphosphate molecules to fill the gap prior to ligation.

A significant problem associated with the rolling circle amplification technique is the occurrence of background amplification. Prior to the advent of the present invention this background amplification was dismissed as primer-induced deletion fragment repeats encompassing a full unit repeat minus the intervening region between 5' ends of the two primers (8). Background amplification represents both a significant problem and a limitation for rolling circle amplification reactions which utilise 2 primers. It is also a major source of false positive results. In fact, the magnitude of the problem presented by the occurrence of this background amplification has been such that it has not been feasible to use the two primer rolling circle amplification techniques with an acceptable level of specificity.

In work leading up to the present invention the inventors have determined the origin of and characterised this background amplification. This class of background amplification has been termed "AmpX". The inventors have determined that it is an alternative amplification reaction which utilizes any linear nucleic acid probe molecules present in the reaction mixture. Typically the reaction products are AmpX multimers of head to tail tandem repeats. However, the inventors have determined that rather than encompassing sequence from the entire circular probe, the products of the AmpX reaction include repeats of a region of the linear target molecule that includes the two primer binding sites, the intervening sequence and some additional sequence of the template molecule flanking the primer binding sites.

Accordingly, the inventors have developed a method for minimizing AmpX background amplification by enriching for closed circular nucleic acid probe molecules prior to their amplification. By conducting the amplification step utilising an enriched population of closed circle nucleic acid probe molecules the incidence of background amplification caused by the AmpX reaction is significantly reduced, thereby enabling more specific rolling circle amplification to occur.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The subject specification contains nucleotide sequence information prepared using the programme PatentIn Version 2.0, presented herein after the bibliography. Each nucleotide sequence is identified in the sequence listing by the numeric indicator <210> followed by the sequence identifier (e.g. <210>1, <210>2, etc). The length, type of sequence (DNA, etc) and source organism for each nucleotide sequence are indicated by information provided in the numeric indicator fields <211>, <212> and <213>, respectively. Nucleotide sequences referred to in the specification are defined by the information provided in numeric indicator field <400> followed by the sequence identifier (e.g. <4001>1, <400>2, etc).

Accordingly, one aspect of the present invention provides a method for amplifying a circular nucleic acid probe produced following interaction of a nucleic acid probe with a target nucleic acid sequence said method comprising enriching said circular nucleic acid probe and subjecting said circular nucleic acid probe to amplification.

Another aspect of the present invention provides a method of rolling circle amplification comprising the steps of facilitating the interaction of a nucleic acid probe with a target nucleic acid sequence; generating a circular nucleic acid probe and enriching for said circular nucleic acid probe; and subjecting said enriched circular nucleic acid probe to amplification.

Still another aspect of the present invention more particularly provides a method of multiple primer rolling circle amplification comprising the steps of facilitating the interaction of a nucleic acid probe with a target nucleic acid sequence; generating a circular nucleic acid probe and enriching for said circular nucleic acid probe; and subjecting said enriched circular nucleic acid probe to amplification.

A further aspect of the present invention provides a method for amplifying a circular nucleic acid probe produced following interaction of a nucleic acid probe with a target nucleic acid sequence said method comprising enzymatically enriching for said circular nucleic acid probe and subjecting said circular nucleic acid probe to amplification.

Still a further aspect of the present invention provides a method of multiple primer rolling circle amplification comprising the steps of facilitating the interaction of a nucleic acid probe with a target nucleic acid sequence; generating a circular nucleic acid probe and enriching for said circular nucleic acid probe by enzymatic enrichment; and subjecting said enriched circular nucleic acid probe to amplification.

Yet another further aspect of the present invention provides a method for amplifying a circular nucleic acid probe produced following interaction of a nucleic acid probe with a target nucleic acid sequence said method comprising non-enzymatically enriching for said circular nucleic acid probe and subjecting said circular nucleic acid probe to amplification.

Still yet another further aspect of the present invention provides a method of multiple primer rolling circle amplification comprising the steps of facilitating the interaction of a nucleic acid probe with a target nucleic acid sequence; generating a circular nucleic acid probe and enriching for said circular nucleic acid probe by non-enzymatic enrichment; and subjecting said enriched circular nucleic acid probe to amplification.

Yet another aspect of the present invention provides a method of multiple primer rolling circle amplification comprising the steps of facilitating the interaction of a nucleic acid probe with a target nucleic acid molecule wherein the terminal regions of said probe form non-contiguous duplexes; generating a circular nucleic acid probe, incorporating a capture ligand into the region intervening said terminal regions and enriching for said circular nucleic acid probe; and subjecting said enriched circular nucleic acid probe to amplification.

Yet a further aspect of the present invention provides a method of multiple primer rolling circle amplification comprising the steps of facilitating the interaction of a nucleic acid probe with a target nucleic acid molecule wherein the terminal regions of said probe form non-contiguous duplexes; generating a circular nucleic acid probe, incorporating a biotinylated capture ligand into the region intervening said terminal regions and enriching for said circular nucleic acid probe; and subjecting said enriched circular nucleic acid probe to amplification.

Another aspect, the present invention is directed to a method of enriching for a circular nucleic acid probe, said method comprising the steps of facilitating the interaction of a nucleic acid probe with a target nucleic acid sequence; and generating a circular nucleic acid probe and enriching for said circular nucleic acid probe.

Yet another aspect of the present invention provides a method of enriching for a circular nucleic acid probe, said method comprising the steps of facilitating the interaction of a nucleic acid probe with a target nucleic acid sequence; and generating a circular nucleic acid probe and enriching for said circular nucleic acid probe by enzymatic enrichment.

Still another aspect of the present invention is directed to a method of enriching for a circular nucleic acid probe, said method comprising the steps of facilitating the interaction of a nucleic acid probe with a target nucleic acid sequence; and generating a circular nucleic acid probe and enriching for said circular nucleic acid probe by non-enzymatic enrichment.

Still yet another aspect of the present invention is directed to a method of enriching for a circular nucleic acid probe, said method comprising the steps of facilitating the interaction of a nucleic acid probe with a target nucleic acid molecule wherein the terminal regions of said probe form non-contiguous duplexes; and generating a circular nucleic acid probe, incorporating a capture ligand into the region intervening said terminal regions and enriching for said circular nucleic acid probe.

In a further aspect there is provided in the method of amplifying a circular nucleic acid probe the improvement comprising amplifying a circular probe produced following interaction of a nucleic acid probe with a target nucleic acid sequence said method comprising enriching for said circular nucleic acid probe and then subjecting said circular nucleic acid probe to amplification.

In another further aspect there is provided in the method of rolling circle amplification the improvement comprising the steps of facilitating the interaction of a nucleic acid probe with a target nucleic acid sequence; generating a circular nucleic acid probe and enriching for said circular nucleic acid probe; and subjecting said enriched circular nucleic acid probe to amplification.

In yet another further aspect there is provided in the method of rolling circle amplification the improvement comprising the steps of facilitating the interaction of a nucleic acid probe with a target nucleic acid sequence; generating a circular nucleic acid probe and enriching for said circular nucleic acid probe by enzymatic enrichment; and subjecting said enriched circular nucleic acid probe to amplification.

In still yet another further aspect there is provided in the method of rolling circle amplification the improvement comprising the steps of facilitating the interaction of a nucleic acid probe with a target nucleic acid sequence; generating a circular nucleic acid probe and enriching for said circular nucleic acid probe by non-enzymatic enrichment; and subjecting said enriched circular nucleic acid probe to amplification.

In another aspect the present invention provides in the method of rolling circle amplification the improvement comprising the steps of facilitating the interaction of a nucleic acid probe with a target nucleic acid molecule wherein the terminal regions of said probe form noncontiguous duplexes; generating a circular nucleic acid probe, incorporating a capture ligand into the region intervening said terminal regions and enriching for said circular nucleic acid probe; and subjecting said enriched circular nucleic acid probe to amplification.

Another aspect of the present invention contemplates a method of diagnosing a disease condition or detecting a genetic variant said method comprising the steps of facilitating the interaction of a nucleic acid probe with a target nucleic acid sequence; generating a circular nucleic acid probe and enriching for said circular nucleic acid probe; and subjecting said enriched circular nucleic acid probe to amplification.

In another aspect the present invention contemplates a method of diagnosing a disease condition or detecting a genetic variant said method comprising the steps of facilitating the interaction of a nucleic acid probe with a target nucleic acid molecular wherein the terminal regions of said probe form non-contiguous duplexes; generating a circular nucleic acid probe, incorporating a capture ligand into the region intervening said terminal regions and enriching for said circular nucleic acid probe; and subjecting said enriched circular nucleic acid probe to amplification.

In still yet another aspect of the present invention is directed to a kit for facilitating rolling circle amplification said kit comprising compartments adapted to contain any one or more of nucleic acid probes, enzymes, capture ligands, means for isolating circular nucleic acid probes and reagents useful for facilitating circularisation, isolation and amplification of said probes. Further compartments may also be included, for example, to receive biological samples.

BRIEF DESCRIPTION OF THE DRAWINGS

FIG. 10 is a photographic representation of RCA reactions on synthetic targets using either unpurified or purified templates. Duplicate sets of ligation reactions were setup at outlined on page 1 (tagged spacer protocols). The oligonucleotides used for this reaction are illustrated diagramatically (FIG. 11). Two separate tubes were included for each reaction set. The negative control reaction (–ve) contained Padlock FV2 and LigW while the positive control reaction (+ve) contained Padlock FV2, LigW and Wildtype target oligonucleotides. Following the initial denaturation at 94° C. for 3 minutes, 1 μL of Ampligase was added to the positive control reactions only. Ligation reactions were carried out at 60° C. for 1 hour. One set of ligations was then purified by the described method. The unpurified and purified ligation reactions were then put through RCA with primers FV3 and FV4 at 60° C. for 1 hour 40 minutes. 10 μL of product from each reaction was electrophoresed through 2% w/v agarose in TBE buffer alongside ϕX174 HaeIII digested DNA marker (lane4 M) and visualised by ethidium bromide staining.

FIG. 11 is a schematic representation of oligonucleotide design used for rolling circle amplification detection of the normal and mutant alleles of the Factor V Leiden gene detection Using RCA. (Padlock FV2: <400>13; LigW Spacer: <400>14; LigM spacer: <400>15; Wildtype target: <400>16; Mutant target: <400>17; Primers: <400>18 and <400>19).

DETAILED DESCRIPTION OF THE INVENTION

Figure 1:
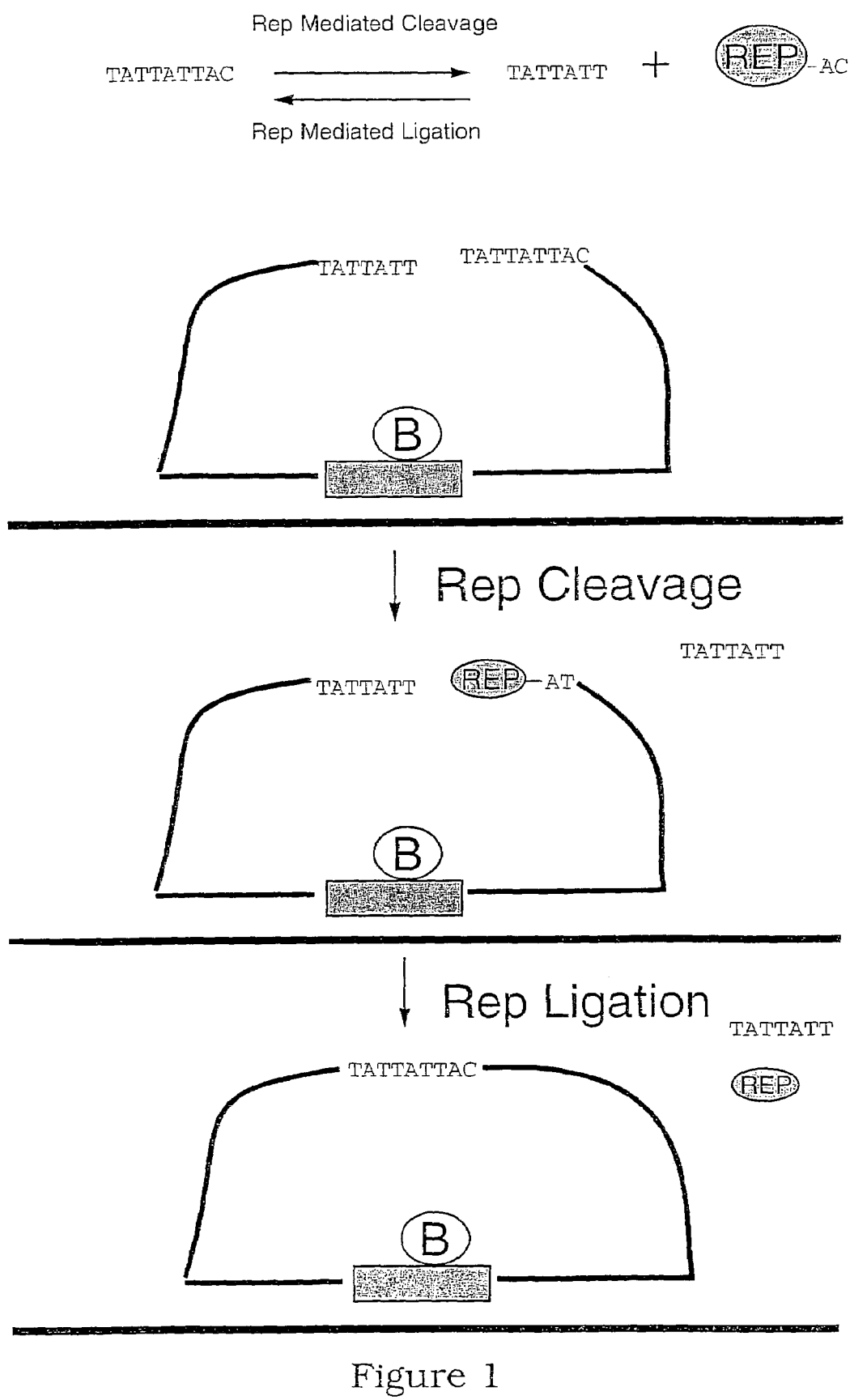
FIG. 1 is a schematic representation of Rep mediated circle ligation.

The present invention is predicated, in part, on the identification of a class of non-specific background amplification reaction which occurs during the amplification of circular probes, such as during rolling circle amplification. This class of non-specific amplification is termed "AmpX" and has been identified by the inventors as occurring due to the presence, in the reaction mixture, of linear nucleic acid probes and open circle nucleic acid probes. Accordingly, the inventors have developed a method of minimising AmpX non-specific amplification by incorporating into the amplification protocol the step of enriching for the closed circular probe molecules prior to their amplification. This step may be achieved, for example, by the purification of closed circle molecules or the removal of linear and/or open circle molecules.

Accordingly, one aspect of the present invention provides a method for amplifying a circular nucleic acid probe produced following interaction of a nucleic acid probe with a target nucleic acid sequence said method comprising enriching for said circular nucleic acid probe and then subjecting said nucleic acid probe to amplification.

It should be understood that the steps of generating a circular nucleic acid probe and the enriching for said probe may be performed in any order. That is, the hybridised probe may be circularised prior to its enrichment or enrichment for the hybridised nucleic acid probe may be performed prior to its circularisation. Further, any one or more steps of the method of the present invention may be performed sequentially or simultaneously.

More particularly, the present invention provides a method of rolling circle amplification comprising the steps of facilitating the interaction of a nucleic acid probe with a target nucleic acid sequence; generating a circular nucleic acid probe and enriching for said circular nucleic acid probe; and subjecting said enriched circular nucleic acid probe to amplification.

Reference to "rolling circle amplification" is not to be taken to refer to a particular form of amplification or a particular amplification protocol. It should be understood to refer to any method of amplifying a circular nucleic acid molecule.

Reference to "interaction" should be understood as a reference to any form of interaction such as hybridisation between complementary nucleotide base pairs or some other form of interaction such as the formation of bonds between any nucleic acid or non-nucleic acid portion of the probe molecule with any nucleic acid or non-nucleic acid portion of the target molecule. The interaction may occur via the formation of bonds such as, but not limited to, covalent bonds, hydrogen bonds, van der Waals forces or any other mechanism of interaction. All references hereinafter to "hybridisation" between two nucleic acid molecules should be understood to encompass any form of interaction between said molecules, for example, where said molecules become associated due to the interaction of non-nucleic acid components of said molecules.

Reference to a "nucleic acid probe" should be understood as a reference to any molecule comprising a sequence of nucleotides, or functional derivatives thereof, the function of which includes the hybridisation of at least one region of said nucleotide sequence with a target nucleic acid sequence. Accordingly, reference to a "target nucleic acid sequence" is a reference to any molecule comprising a sequence of nucleotides or functional derivatives thereof which molecule is a molecule of interest and is therefore the subject of identification via a probing step. Both the nucleic acid probe and the target nucleic acid sequence may comprise non-nucleic acid components. For example, the nucleic acid probe may also comprise a non-nucleic acid detection tag or some other non-nucleic acid component which facilitates the functioning of the molecule. Similarly, the target nucleic acid sequence may comprise a non-nucleic acid component. For example, the target nucleic acid sequence may be bound to an antibody. This may occur, for example, where the target nucleic acid sequence is present in a biological sample isolated from an individual who is mounting an immune response, such as an autoimmune response, to said target nucleic acid sequence. In another example, the nucleic acid probe may be a protein nucleic acid which comprises a peptide backbone exhibiting nucleic acid side chains.

The term "nucleic acid probe" should also be understood to encompass reference to two or more nucleotide sequence molecules which are ligated, associated or otherwise joined such that they form a single nucleotide sequence molecule which ligation or other form of joining is performed either during or after probing of the target sequence with the nucleic acid probe. Accordingly, facilitation of the ligation or other form of association of the nucleotide sequence molecules may be performed at any time during or after probing of the target sequence such as before, during or after hybridisation of the nucleic acid probe to the target sequence. For example, in the Rep mediated system of ligation (an example of which is represented schematically in FIG. 1), a target sequence is probed with two nucleic acid molecules. A first probe molecule comprises a terminal TATTATT sequence while a second probe molecule comprises a terminal TATTATTAC sequence. Following hybridisation of these probes to the target sequence, the Rep molecule is utilised to facilitate cleavage of the TATTATT component of the terminal TATTATTAC of said second probe molecule followed by ligation of the terminal AC of said second probe molecule to the terminal TATTATT component of a first probe molecule which has hybridised to the target sequence, for example, at a position adjacent to said second probe molecule.

The nucleic acid probe is preferably a single stranded nucleotide sequence and may have any conformation including, for example, a linear conformation or an open circle confirmation, that is, where the nucleotide probe is substantially circular in shape but its terminal regions do not connect. Reference to the "terminal regions" of the nucleic acid probe is a reference to the region located at each end of the nucleic acid probe. The nucleic acid probe preferably comprises two discrete target probe regions located one at each terminal region of the nucleic acid probe. However, it should be understood that the target probe regions are not necessarily located at the terminal regions of the nucleic acid probe and may be located at any other suitable region of the nucleic acid probe. The target probe region is the region of nucleotides complementary to one or more nucleotide sequence regions of the target nucleic acid sequence of interest. The nucleotide sequence region located between the terminal regions of the nucleic acid probe also preferably comprises at least one primer region. The "primer region" is a reference to the sequence of nucleotides which are designed to interact with at least part of a primer. Reference to the "primer region" also encompasses reference to any sequence of nucleotides to which a sense primer corresponds. Those skilled in the art will understand that the primer is a molecule comprising a nucleotide sequence which interacts with a region of a target nucleic acid sequence and from which complementary nucleotide synthesis, for example utilising a polymerase such as DNA polymerase, is initiated. The interaction of a primer with a primer region may occur by any suitable means such as, but not limited to, hybridisation of complementary base pairs or the interaction of non-nucleic acid components comprising the primer and the primer region. The nucleic acid probe may also optionally comprise regions corresponding to replication of origins, promotors, nucleic acid and/or non-nucleic acid detection tags.

In one embodiment of the present invention, the nucleic acid probe comprises two target probe regions and two primer regions wherein exponential amplification of the circular nucleic acid probe is achieved due to the interaction of a first primer with a primer region of the nucleic acid probe and a second primer which interacts with a region of the nucleic acid probe complementary strand which is synthesised following interaction of the first primer with the probe. This method of rolling circle amplification is herein referred to as "two primer rolling circle amplification".

The primers, according to the method of the present invention, may function by any suitable means. For example, the first primer may be designed to interact via complementary base pairing with a primer region of the nucleic acid probe. This type of primer is commonly referred to as a complementary primer and facilitates the synthesis of a nucleic acid strand complementary to the nucleic acid probe. The second primer may be designed as a sense primer which corresponds to a second primer region of the nucleic acid probe thereby facilitating the synthesis of a nucleic acid strand complementary to the strand synthesised utilising the first primer. Alternatively, a single primer nucleotide sequence may be used which primer recognises two or more distinct primer regions of the nucleic acid probe. In this regard, the primer regions may be of complementary nucleotide sequence orientation. In still yet another example, one or more of the primers may comprise a non-nucleic acid component which interacts with a nucleic acid or non-nucleic acid component at a primer region thereby facilitating the synthesis of a complementary nucleic acid strand. It should be understood that the method of the present invention extends to amplification which utilises more that two primers (referred to herein as "multiple primer amplification"). For example, two or more complementary primers directed to discrete primer regions and two or more sense primers directed to discrete primer regions. "Multiple primer amplification" should be understood to include the use of a single sequence which recognises two or more distinct primer regions of a nucleic acid probe.

Accordingly, the present invention more particularly provides a method of multiple primer rolling circle amplification comprising the steps of facilitating the interaction of a nucleic acid probe with a target nucleic acid sequence; generating a circular nucleic acid probe and enriching for said circular nucleic acid probe; and subjecting said enriched circular nucleic acid probe to amplification.

Preferably, the multiple primer rolling circular amplification is two primer rolling circle amplification.

Reference to a "nucleic acid" should be understood as a reference to both deoxyribonucleic acid and ribonucleic acid or derivatives thereof. The nucleic acid molecules utilised in the method of the present invention may be of any origin including naturally occurring (for example a biological sample may be utilised), recombinantly produced or synthetically produced. Where a biological sample is utilised, for example as a potential source of target nucleic acid sequence, the nucleic acid component may optionally be extracted from the sample prior to testing (for example for the purpose of coupling it to a solid phase such as paper). This is not essential, though, and the method of the present invention may be performed utilising, for example, blood samples or it may be performed in situ with a biopsy specimen.

Reference to "derivatives" should be understood to include reference to fragments, parts, portions, chemical equivalents, analogues, mutants, homologous and mimetics from natural, synthetic or recombinant sources. "Functional derivatives" should be understood as derivatives which exhibit any one or more of the functional activities of nucleotides or nucleic acid sequences. The derivatives of said nucleotides or nucleic acid sequences include fragments having particular epitopes or parts of the nucleotide or nucleic acid sequence fused to other proteinaceous or non-proteinaceous molecules. Analogs contemplated herein include, but are not limited to, modifications to the nucleotide or nucleic acid sequence such as modifications to its chemical makeup or overall conformation. This includes, for example, modification to the manner in which nucleotides or nucleic acid sequences interact with other nucleotides or nucleic acid sequences such as at the level of backbone formation or complementary base pair hybridisation. The biotinylation of a nucleotide or nucleic acid sequence is an example of a "functional derivative" as herein defined. Derivatives of nucleic acid sequences may be derived from single or multiple nucleotide substitutions, deletions and/or additions. The term "functional derivatives" should also be understood to encompass nucleotides or nucleic acid sequences exhibiting any one or more of the functional activities of a nucleotide or nucleic acid sequence, such as for example, products obtained following natural product screening.

Facilitating the interaction of the nucleic acid probe with the target nucleic acid sequence may be performed by any suitable method. Those methods will be known to those skilled in the art.

Where the target probe regions interact with a target nucleic acid sequence, the nucleic acid probe assumes an open circle conformation (herein referred to as an "open circle nucleic acid probe"). By interacting with a target nucleic acid sequence, the target probe regions generally form two discrete duplex regions due, for example, to complementary nucleotide base pairing between the nucleotides of the target nucleic acid sequence and the nucleotides of the target probe region of the nucleic acid probe (referred to herein as "duplexes"). These two duplexes exist non-contiguously due to the absence of a bond, such as the phosphodiester bond, between the terminal nucleotide at the 5' end of the nucleic acid probe and the terminal nucleotide at the 3' end of the nucleic acid probe. There may also exist an intervening region of nucleotides, of target nucleic acid sequence origin, between the duplexes. This intervening region of nucleotides may comprise any number of nucleotides.

Reference to an "open circle nucleic acid probe" should be understood to also encompass the formation of a single open circle configuration which comprise two or more nucleic acid probes. For example, a double open circle nucleic acid probe (which is encompassed within the meaning of "open circle nucleic acid probe") is formed where:
  (i) the 5' target probe region of a first nucleic acid probe hybridises to a first target nucleic acid sequence molecule and the 3' target probe region of said probe hybridises to a second target nucleic acid sequence molecule; and
  (ii) the 3' target probe region of a second nucleic acid probe hybridises to said first target nucleic acid sequence and the 5' target probe region of said second probe hybridises to said second target nucleic acid sequence.

Said first and second target nucleic acid sequences may be identical or different. A double open circle nucleic acid probe therefore exhibits two pairs of non-contiguous duplexes. One is located on the first target nucleic acid sequence and one is located at the second target nucleic acid sequence. Open circle probes of this type operate similarly to the single probes and yield identical products. These multiple open circle nucleic acid probes are circularised and enriched for in the same manner as open circle probes comprising only a single probe. In fact, any given reaction mixture is likely to comprise open circle nucleic acid probes of both single probe and multiple probe (such as a double probe) types.

To permit amplification of the nucleic acid probe, the open circle nucleic acid probe which has interacted with the target sequence at the duplex regions requires circularisation. By "circularisation" is meant the formation of a closed circle. Circularisation may be performed by any one of a number of methods including, but not limited to, gap-filling or spacer oligonucleotide ligation. Reference to "gap-filling" is a reference to the circularisation of an open circle nucleic acid probe via the synthesis of a nucleotide sequence to link the terminal ends of the open circle nucleic acid probe. In this regard, the open circle nucleic acid probe is reacted with the required dNTP's, ligase and DNA polymerase. By "spacer oligonucleotide ligation" is meant the insertion of one or more previously synthesised nucleotide sequences (referred to as "spacer oligonucleotides") into the gap between the 5' and 3' ends of the open circle nucleic acid probe. The ends of the spacer are then ligated with the ends of the open circle nucleic acid probe using, for example, the ligase enzyme. Where more than one spacer oligonucleotide is utilised they may be, for example, ligated in tandem to fill the gap between 5' and 3' ends of the open circle nucleic acid probe.

Upon circularisation of the open circle nucleic acid probe, the now contiguous duplex will generally assume a helical formation. This essentially twists the hybridised portion of the probe around the target nucleic acid sequences resulting in "locking" of the circularised probe around the target nucleic acid sequence. This "locking" is often referred to as "padlock formation" or "padlock circularisation". Accordingly, reference to a circular nucleic acid probe should be understood to include reference to both padlock and non-padlock probes.

Without limiting the present invention to any one theory or mode of action, following circularisation of the open circle nucleic acid probe, the reaction mixture will usually comprise, in various ratios, the circularised nucleic acid probe (also referred to as a "closed circle nucleic acid probe"), open circle nucleic acid probes and linear nucleic acid probes. The linear nucleic acid probes are those probes which did not interact with or did not ligate to a target nucleic acid sequence. Following circularisation, any remaining open circle nucleic acid probes will include both those probes which are unaltered by the circularisation step and those probes which were incompletely circularised, for example, where the spacer ligated to only one of the nucleic acid probe ends (ie. either the 5' or the 3' end) or where the gap-fill synthesis was only partially completed. Where two primer rolling circle amplification is performed using such a reaction mixture, the resultant amplification products will include:
  (i) a nucleic acid sequence synthesised from the first primer. This nucleotide sequence will comprise tandem repeats of a sequence complementary to that of the closed circle nucleic acid probe; and
  (ii) a nucleotide sequence synthesised from the second primer. This nucleotide sequence will comprise tandem repeats of a nucleic acid sequence complementary to the nucleic acid sequence generated by the first primer.

These amplification products may exist as single stranded nucleic acid sequences or at nucleic acid sequences either completely or partially hybridised to a complementary nucleic acid sequence. By "partial hybridisation" is meant that part of the nucleic acid sequence is hybridised to a complementary sequence and part of the nucleic acid sequence is in single stranded form. This will occur, for example, due to the effects of strand displacement such as where primers have interacted with two or more of the tandem repeats of a nucleic acid sequence and the amplification product synthesised from a downstream primer encounters the adjacent upstream primer. In this case, the amplification primer generated from the downstream product will displace the upstream primer as it continues its complementary synthesis extension.

However, in addition to amplification products (i) and (ii) above, the inventors have characterized a previously unidentified background amplification product, termed the AmpX reaction, which is also produced. This amplification product is usually a nucleotide sequence comprising one or more tandem repeats complementary to the probe sequence but stretching from the first primer region to the second primer region and including the first and second primer regions. These tandem repeats may, however, also comprise extra nucleotide sequence flanking the downstream primer site and/or deletions in the nucleotide sequence. This reaction occurs in the presence of open circle or linear nucleic acid probes. The precise mechanism by which this AmpX reaction occurs is unknown, however it is thought to involve some form of illegitimate priming and strand invasion events of the open circle or linear nucleic acid probes.

Still without limiting the present invention to any one theory or mode of action, the inventors have developed a method of amplifying a circular nucleic acid molecule which method incorporates an enrichment step which is performed following interaction of the nucleic acid probe to the target nucleic acid sequence but prior to the amplification of the probe. The enrichment step may be performed either before or after the formation of closed circle probes.

Reference to "enriching" should be understood as a reference to increasing the ratio of closed circle nucleic acid probes relative to the linear nucleic acid molecules. This can be achieved, for example, by degrading, removing, inactivating or otherwise reducing the linear nucleic acid molecules (such as linear nucleic acid probes and/or linear target sequences) or by specifically isolating the closed circle nucleic acid probes from the reaction mixture.

Enriching for closed circle nucleic acid probes can be achieved by any one of a number of methods including, but not limited to, electrophonetic separation, chromatographic separation (for example by size exclusion or affinity chromatography) or degrading the linear nucleic acid molecules utilising, for example an enzyme such as an exonuclease (referred to herein as "enzymatic enrichment"). Without limiting the present invention to any one theory or mode of action, exonucleases function by cleaving the terminal nucleotides from a linear nucleic acid molecule. Closed circle nucleic acid probes are not degraded and thereby undergo enrichment. For example, linear and/or open circle molecules may be digested utilising the enzyme exonuclease III which functions by degrading free DNA termini but does not degrade closed circle molecules. This step enriches for closed circle molecules by selectively removing linear and/or open circle molecules and is preferably performed after the circularization step but prior to the amplification step. Enzymatic enrichment is particularly useful for achieving enrichment of closed circle nucleic acid probes by reducing the population of linear and/or open circle nucleotide sequences.

Accordingly, in one embodiment the present invention provides a method for amplifying a circular nucleic acid probe produced following interaction of a nucleic acid probe with a target nucleic acid sequence said method comprising enzymatically enriching generation of a circular nucleic acid probe and enzymatic enrichment for said circular nucleic acid probe and subjecting said circular nucleic acid probe to amplification.

More particularly, the present invention provides a method of multiple primer rolling circle amplification comprising the steps of facilitating the interaction of a nucleic acid probe with a target nucleic acid sequence; generating a circular nucleic acid probe and enriching for said circular nucleic acid probe by enzymatic enrichment; and subjecting said enriched circular nucleic acid probe to amplification.

Preferably, said enzymatic enrichment is performed utilising an exonuclease.

In addition to enzymatic enrichment, closed circle nucleic acid probes can be enriched for utilising non-enzymatic methods. Examples of non-enzymatic methods suitable for use in the method of the present invention include, but are not limited to, electrophonetic separation, chromatographic separation (for example by size exclusion or affinity chromatography) or the introduction of a capture ligand into the closed circle probes via which the closed circle probes can thereby be isolated. Methods such as electrophonetic or chromatographic separation may be designed, for example, reduce the proportion of linear nucleic acid molecules while the use of a capture ligand is particularly useful for facilitating the isolation of closed circle nucleic acid probes. The capture ligand may be introduced, during circularisation, into the region intervening the terminal ends of the open circle probe. However it should be understood that the present invention is not limited to the introduction of a capture ligand by this particular method. In this regard, the capture ligand may be introduced into other regions of the nucleic acid probe such that it facilitates the isolation of closed circle nucleic acid probes.

Accordingly, in another embodiment the present invention provides a method for amplifying a circular nucleic acid probe produced following interaction of a nucleic acid probe with a target nucleic acid sequence said method comprising non-enzymatically enriching for said circular nucleic acid probe and subjecting said circular nucleic acid probe to amplification.

More particularly, the present invention provides a method of multiple primer rolling circle amplification comprising the steps of facilitating the interaction of a nucleic acid probe with a target nucleic acid sequence; generating a circular nucleic acid probe and enriching for said circular nucleic acid probe by non-enzymatic enrichment; and subjecting said enriched circular nucleic acid probe to amplification.

Still more particularly, the present invention provides a method of multiple primer rolling circle amplification comprising the steps of facilitating the interaction of a nucleic acid probe with a target nucleic acid molecule wherein the terminal regions of said probe form non-contiguous duplexes; generating a circular nucleic acid probe, incorporating a capture ligand into the region intervening said terminal regions and enriching for said circular nucleic acid probe; and subjecting said enriched circular nucleic acid probe to amplification.

Figure 2:
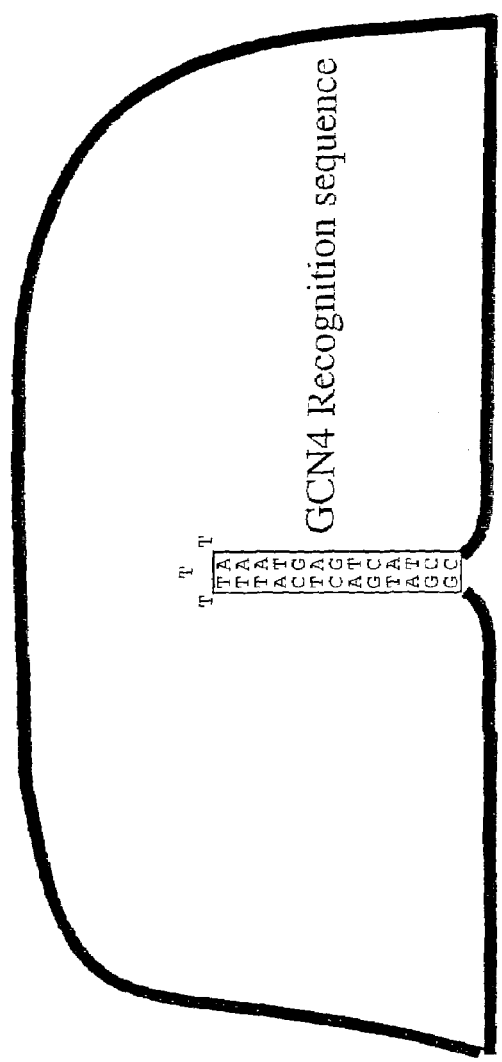
FIG. 2 is a schematic representation of a nucleic acid probe incorporating a GCN4 recognition sequence (<400>26).
Figure 3:
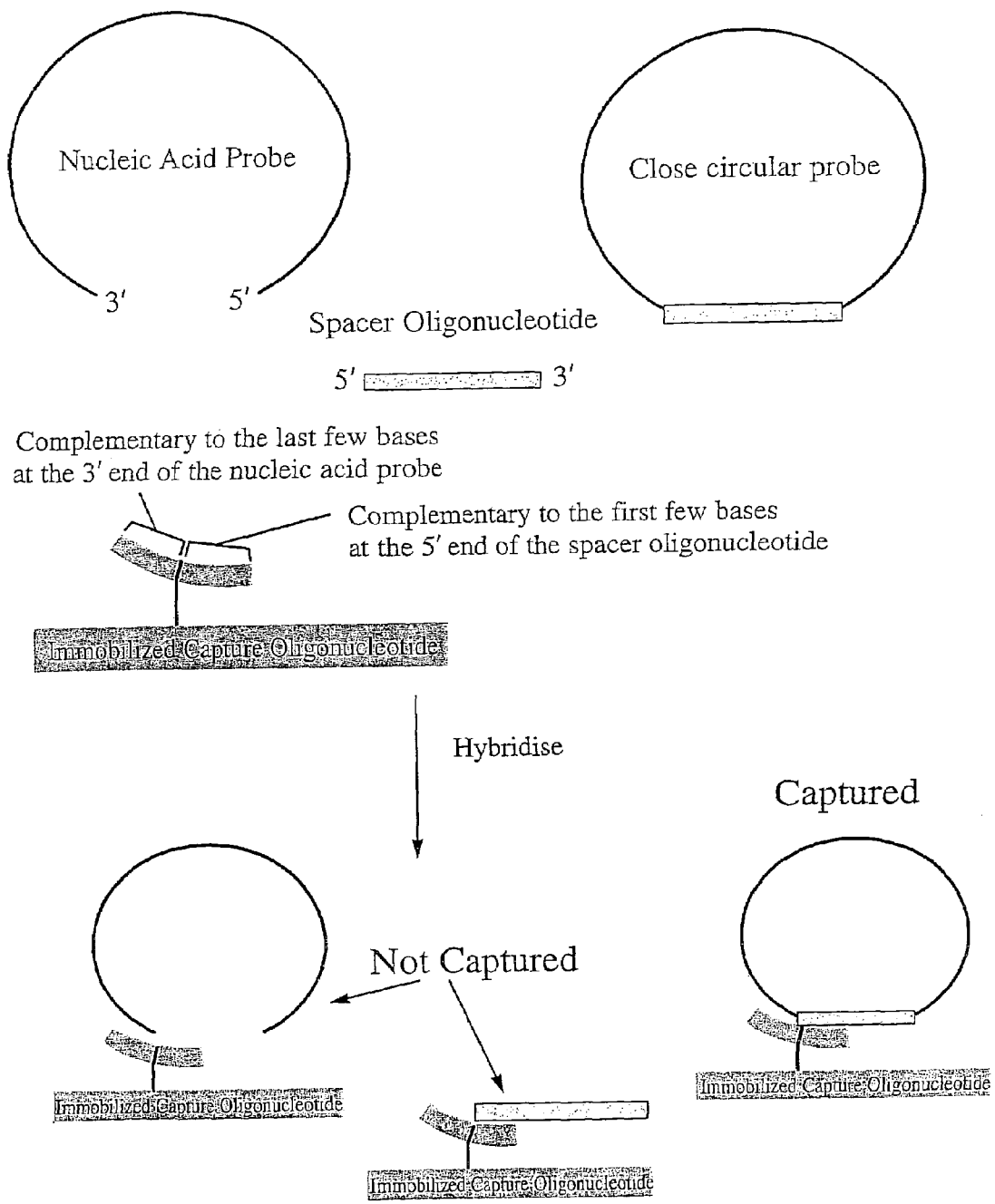
FIG. 3 is a schematic representation of capture by differential hybridisation.

By "capture ligand" is meant a molecule which permits the selective isolation of a nucleic acid probe into which it is incorporated. It may be incorporated by any suitable means. The capture ligand may take the form of modified nucleotides which are used to link the 5' and 3' terminal nucleotides of the open circle nucleic acid probe (by either gap-filling or spacer oligonucleotide ligation, for example) or it may comprise unmodified nucleic acids (such as a nucleic acid tag), the sequence of which facilitates isolation of probe molecules incorporating the nucleic acid tag. For example, the capture ligand may be a nucleotide sequence which comprises the GCN4 recognition sequence (refer FIG. 2). In another example, a nucleotide sequence capture ligand may be introduced which sequence permits the isolation of closed circle nucleic acid probes by differential hybridisation potential. One example of this method of enrichment is schematically depicted in FIG. 3. In this example, the enrichment step is achieved via solid phase capture. However, it should be understood that this method is not limited to solid phase capture.

The capture ligand may therefore itself both permit selective purification and act to circularise the open circle probe. For example, the capture ligand may be an oligonucleotide comprising nucleotide analogues which are ligated into the intervening region. In this case, the oligonucleotide acts to circularise the open circle probe and by virtue of the modified nucleotides of which it is synthesised, permits selective purification of the probe by virtue of the modification. Alternatively, the nucleotide analogues may be introduced into the reaction mixture comprising the open circle probes as dNTP analogues which by gap-fill synthesis circularise the open circle probe.

The capture ligand may alternatively take the form of a nucleic acid molecule or a nucleotide to which a capture molecule is linked, bound or otherwise associated which nucleic acid molecule or nucleotide will link the 5' and 3' terminal nucleotides of the open circle nucleic acid probe. The present invention should be understood to extend to the use of any suitable molecule to comprise the capture ligand via its association with one or more linking nucleotides. For example, magnetic beads which are coupled to a gap-fill oligonucleotide are envisaged as are molecules such as a hapten which can be bound by an antibody.

Preferably, the capture ligand is one which is resistant to the denaturing conditions which are applied to the reaction mixture to achieve breaking of the hydrogen bonds of the duplexes. This step is usually performed to free open circle nucleic acid probes which may co-purify with the target molecules during the enrichment step. In one embodiment, the capture ligand comprises a biotinylated oligonucleotide. Following ligation of this oligonucleotide into the open circle nucleic acid probe a closed circle nucleic acid probe is formed. The closed circle probe can be isolated by binding the biotin molecule which is coupled to the ligated oligonucleotide to streptavidin.

Enrichment of the closed circle probes incorporating a capture ligand may be achieved by any suitable method such as, but not limited to, the cross linking and precipitation of the closed circular nucleic acid probes comprising the capture ligand or coupling of the closed circular probes to a solid phase via the capture ligand.

Accordingly one embodiment of the present invention provides a method of multiple primer rolling circle amplification comprising the steps of facilitating the interaction of a nucleic acid probe with a target nucleic acid molecule wherein the terminal regions of said probe form non-contiguous duplexes; generating a circular nucleic acid probe, incorporating a biotinylated capture ligand into the region intervening said terminal regions and enriching for said circular nucleic acid probe; and subjecting said enriched circular nucleic acid probe to amplification.

Following enrichment of the circular nucleic acid probe, the circular probe may be subjected to amplification according to methods well known to those skilled in the art. Without limiting this aspect of the present invention in any way, amplification may be performed by initiating nucleotide extension from a primer complementary to a portion of the circular probe. Through the use of strand-displacing DNA polymerases this extension reaction produces large tandemly arranged multimeric single-stranded DNA products, complementary to the circular target. This occurs due to continual displacement of any nucleic acid downstream of the rapidly extending 3' end of the new strand. This reaction in itself allows linear amplification of DNA from the circular probes but the size of the molecules produced and the level of amplification obtained is limited by the processivity of the strand-displacing DNA polymerase. To achieve exponential amplification kinetics under isothermal conditions a second oligonucleotide primer is used. The multimeric polymers that are produced from the initial priming events on the circular probes comprise multiple primer binding sites for this second primer, thereby facilitating the simultaneous initiation of multiple DNA strand synthesis. Because of the nature of the strand-displacing polymerases and the simultaneous initiation of multiple strand synthesis on a single multimeric polymer, the resultant product is a network of highly branched strands elongating and displacing down the length of the multimeric polymers. The original primer complementary to the circular probe can also prime these displaced strands. This molecular cascade then continues until there are no more primable sites or until one of the substrates for the reaction is depleted. It is also thought that the completely displaced strands themselves may act as primers by interacting with other displaced strands. This results in significantly greater amplification than is obtainable by traditional nucleic acid amplification techniques.

It should be understood that the method of the present invention does not necessarily selectively isolate only closed circle nucleic acid probes from the reaction mixture. Rather, it is a method for enriching for closed circular probes. For example, where a circularised probe is in a padlock conformation around a target sequence, isolation of the probe may also isolate the target sequence due to the padlock conformation.

Following amplification of the closed circle probes, the amplification products may optionally be detected using a wide variety of techniques including, but not limited to, staining of the products with intercalating dyes, the incorporation of detection tags directly into the products or they can be coupled with a variety of other detection molecules which are known to those skilled in the art. These could include, but should not be limited to, radioactive isotopes, fluorescent molecules, phosphorescent molecules, enzymes, antibodies and ligands.

Figure 4:
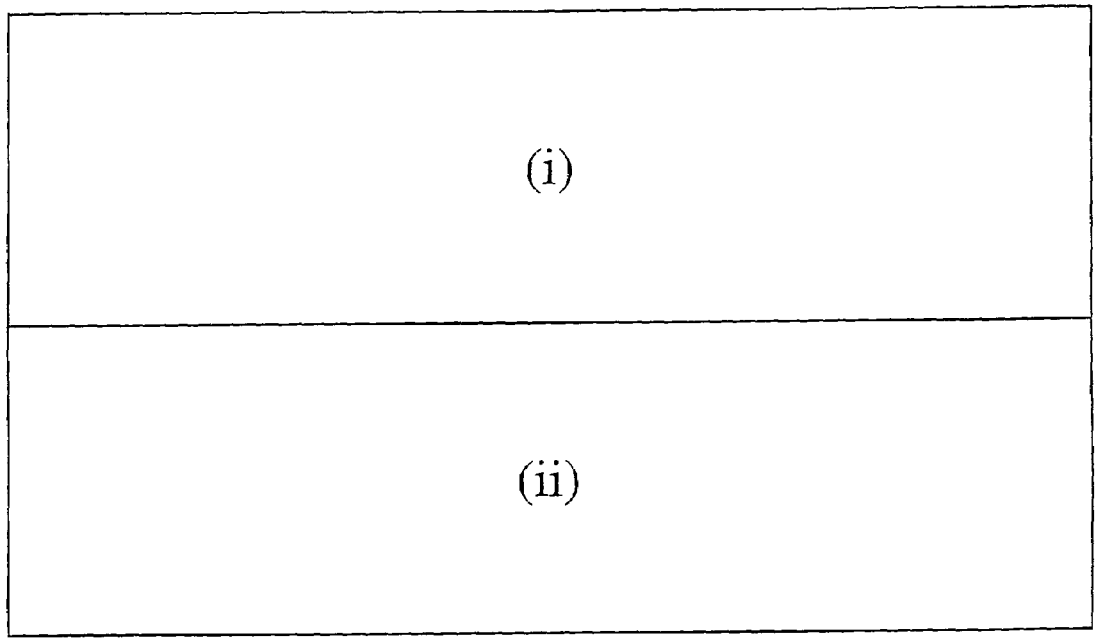
FIG. 4 is schematic representation of padlock FV2. <400>13 depicts the padlock FV-2 sequence and <400>14 the LigW spacer. <400>16 depicts the Wildtype target and <400>24 and <400>25 the amplification primers.

In one example, the detection of amplified products could include the solid phase-based amplification using rolling circle amplification. In this example one of the amplification primers is coupled to a solid support. This solid support may be any solid material to which oligonucleotides can be coupled. Such materials are known to those skilled in the art. These materials may be incorporated into multiple formats which include but shall not be limited to magnetic beads, microtitre trays, membranes and dipsticks. The second primer used in the amplification reaction contains a molecular tag (e.g. fluorescein). Alternatively, a molecular tag such as biotin, DIG or a fluorophore may be incorporated in the form of labelled nucleotides during the synthesis of amplified DNA. During the amplification reaction if both primers are used for rolling circle amplification some of the products will be coupled directly to the surface of the solid support. Furthermore these products will be labelled due to priming from the second primer containing the molecular tag. Unused primers and other by-products of the reaction can therefore be directly washed from the solid support without disrupting the attached amplified products. The attached products can then be identified utilising the molecular tag. Primers used in one example of this amplification are schematically depicted in FIG. 4.

In another example, the present invention should be understood to extend to the application of rolling circle amplification in the context of DNA microarrays.

In another aspect, the present invention is directed to a method of enriching for a circular nucleic acid probe, said method comprising the steps of facilitating the interaction of a nucleic acid probe with a target nucleic acid sequence; and generating a circular nucleic acid probe and enriching for said circular nucleic acid probe.

In one embodiment the present invention provides a method of enriching for a circular nucleic acid probe, said method comprising the steps of facilitating the interaction of a nucleic acid probe with a target nucleic acid sequence; and generating a circular nucleic acid probe and enriching for said circular nucleic acid probe by enzymatic enrichment.

In another embodiment the present invention is directed to a method of enriching for a circular nucleic acid probe, said method comprising the steps of facilitating the interaction of a nucleic acid probe with a target nucleic acid sequence; and generating a circular nucleic acid probe and enriching for said circular nucleic acid probe by non-enzymatic enrichment.

Still more particularly, the present invention is directed to a method of enriching for a circular nucleic acid probe, said method comprising the steps of facilitating the interaction of a nucleic acid probe with a target nucleic acid molecule wherein the terminal regions of said probe form non-contiguous duplexes; and generating a circular nucleic acid probe, incorporating a capture ligand into the region intervening said terminal regions and enriching for said circular nucleic acid probe.

Most particularly said capture ligand is a biotinylated nucleotide.

In yet another aspect there is provided in the method of amplifying a circular nucleic acid probe the improvement comprising amplifying said circular probe produced following interaction of a nucleic acid probe with a target nucleic acid sequence said method comprising enriching for said circular nucleic acid probe and then subjecting said circular nucleic acid probe to amplification.

Preferably there is provided in the method of rolling circle amplification the improvement comprising the steps of facilitating the interaction of a nucleic acid probe with a target nucleic acid sequence; generating a circular nucleic acid probe and enriching for said circular nucleic acid probe; and subjecting said enriched circular nucleic acid probe to amplification.

In one embodiment of this aspect of the present invention there is provided in the method of rolling circle amplification the improvement comprising the steps of facilitating the interaction of a nucleic acid probe with a target nucleic acid sequence; generating a circular nucleic acid probe and enriching for said circular nucleic acid probe by enzymatic enrichment; and subjecting said enriched circular nucleic acid probe to amplification.

In another aspect of the present invention there is provided in the method of rolling circle amplification the improvement comprising the steps of facilitating the interaction of a nucleic acid probe with a target nucleic acid sequence; generating a circular nucleic acid probe and enriching for said circular nucleic acid probe by non-enzymatic enrichment; and subjecting said enriched circular nucleic acid probe to amplification.

More particularly, the present invention provides in the method of rolling circle amplification the improvement comprising the steps of facilitating the interaction of a nucleic acid probe with a target nucleic acid molecule wherein the terminal regions of said probe form non-contiguous duplexes; generating a circular nucleic acid probe, incorporating a capture ligand into the region intervening said terminal regions and enriching for said circular nucleic acid probe; and subjecting said enriched circular nucleic acid probe to amplification.

Most particularly said capture ligand is a biotinylated nucleotide.

The nucleic acid sequences of the present invention may be derived from the human genome but genomes and nucleotide sequences from non-human animals and plants, microbes (for example, bacteria, parasites or yeast), viruses and prion sequences are also encompassed by the present invention. Non-human animals contemplated by the present invention include primates, livestock animals (eg. sheep, cows, pigs, goats, horses, donkeys), laboratory test animals (eg. mice, rats, guinea pigs, hamsters, rabbits), domestic companion animals (eg. dogs, cats), birds (eg. chickens, geese, ducks and other poultry birds, game birds, emus, ostriches) and captive wild or tamed animals (eg. foxes, kangaroos, dingoes). It should be understood that the process of the present invention may be homologous or heterologous with respect to the species from which the nucleic acid molecules are derived. A "homologous" process is one where all the nucleic acid molecules utilised in the method of the present invention are derived from the same species. A "heterologous" process is one where at least one of the nucleic acid molecules is from a species different to that of other of the nucleic acid molecules. It should also be understood that in many cases, any given nucleic acid molecule (such as the nucleic acid probe) will not have been derived from any species but will have been designed to comprise a sequence of nucleotides which are not naturally occurring. Individual regions of the probe may be based on naturally occurring sequences derived from one or more species (for example a promoter region or a target probe region).

The method of the present invention is useful for improving the specificity of isothermic amplification. This includes, for example, improving the specificity of the generation of tandem compliments of the closed circle nucleic acid probe sequences that are generated by strand displacement synthesis. The present invention is also useful in diagnostic applications such as the detection, identification, quantitation and/or typing of specific genetic sequences found in biological or environmental samples such as molecular sequences from human, animal, plant, parasite, bacterial or viral origin. This includes, but is not limited to, allelic discrimination, identification of genetic variants (for example, for the purpose of predicting patient drug responses), identification of simple nucleotide polymorphisms and multiplex detection of strand displacement products wherein, for example, the amplified tandemers are detected using multi colour coding probes that allow the separate, simultaneous and quantitative detection of multiple different amplified target sequences. Further, the present invention is useful with respect to the diagnosis of genetic or infectious diseases such as bacterial and viral infections. In this regard, one application of the present invention is the probing of biological samples (such as blood, urine, mucus or biopsy specimens) to detect the presence of bacteria or virus wherein the bacterium or virus comprises the target nucleic acid sequence to which the target probe regions of the nucleic acid probe are directed.

Accordingly, yet another aspect of the present invention contemplates a method of diagnosing a disease condition or detecting a genetic variant said method comprising the steps of facilitating the interaction of a nucleic acid probe with a target nucleic acid sequence; generating a circular nucleic acid probe and enriching for said circular nucleic acid probe; and subjecting said enriched circular nucleic acid probe to amplification.

In one preferred embodiment said enriching step is non-enzymatic enrichment.

In another preferred embodiment said enriching step is an enzymatic enrichment step.

According to this preferred embodiment the present invention contemplates a method of diagnosing a disease condition or detecting a genetic variant said method comprising the steps of facilitating the interaction of a nucleic acid probe with a target nucleic acid molecule wherein the terminal regions of said probe form non-contiguous duplexes; generating a circular nucleic acid probe, incorporating a capture ligand into the region intervening said terminal regions and enriching for said circular nucleic acid probe; and subjecting said enriched circular nucleic acid probe to amplification.

Said target molecule may be present in a biological sample. Accordingly, the biological sample may be directly tested or else all or some of the nucleic acid material present in the biological sample may be isolated prior to testing. It is within the scope of the present invention for the target nucleic acid sequence to be pre-treated prior to testing, for example, inactivation of live virus.

The method of the present invention is also useful for generating nucleic acid products such as, but not limited to, dendrimeric probes, molecular weight markers, immobilised ligands for affinity chromatography of transcription factors and products for use in the functional analysis of transactivating factors and Southwestern blot analysis.

Figure 19:
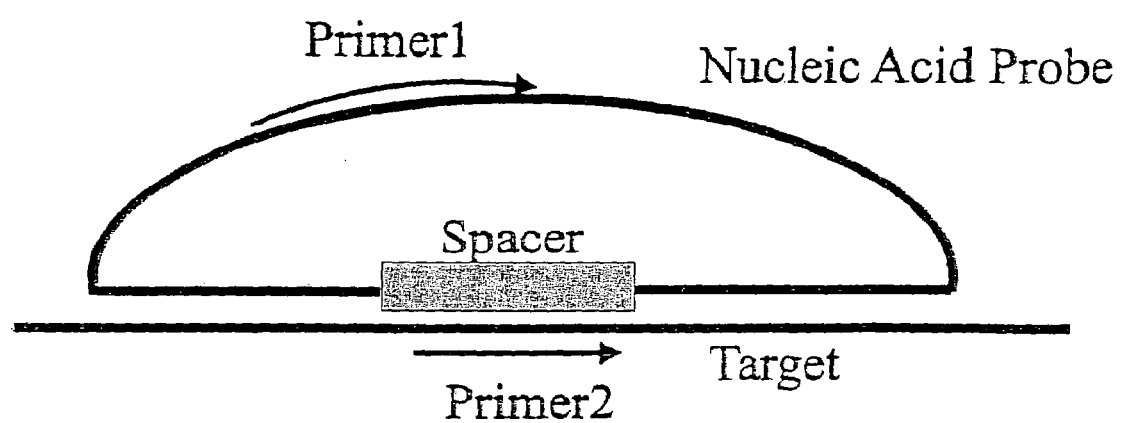
FIG. 19 is a schematic representation of a padlock probe designed such that no two primers bind to any one oligonucleotide.

Since the AmpX background amplification problem occurs due to a reaction that takes place when two or more primers can bind to the linear nucleic acid probes, another aspect of the present invention is directed to a method of amplifying circular nucleic acid probes by designing these probes such that no two primers bind to any one oligonucleotide. Accordingly, no purification of the ligation reaction is necessary. One example of a suitably designed nucleic acid probe and primers are schematically illustrated in FIG. 19.

Still yet another aspect of the present invention is directed to a kit for facilitating amplification of a circular nucleic acid probe said kit comprising compartments adapted to contain any one or more of nucleic acid probes, enzymes, capture ligands, means for isolating circular nucleic acid probes and reagents useful for facilitating circularisation, isolation and amplification of said probes. Further compartments may also be included, for example, to receive biological samples.

Preferably said amplification is rolling circle amplification.

Further features of the present invention are more fully described in the following non limiting figures and/or examples. It is to be understood, however, that this detailed description is included solely for the purpose of exemplifying the present invention.

EXAMPLE 1

AmpX Analysis—Materials

Bacterial Strains

E. coli strain PNG801 is a derivative of the E. coli K12 wildtype strain W1485 (obtained from N. Kleckner, Harvard University). The mini-transposon Tn10 (No. 103), encoding a kanamycin resistance gene was introduced into E. coli strain W1485 (10). From the resulting kanamycin resistant poolate one strain was selected and named PNG801. E. coli DH5α which has been described previously (Gibco, BRL) was used as a negative control, representing an E. coli genome not containing the mini-transposon. Genomic DNA was extracted from both E. coli strains (11) and resuspended in TE buffer.

Primers

Oligonucleotides were purchased from Bresatec and Gibco BRL and synthesized using standard phosphoramidite chemistry. Oligonucleotides used as templates in the amplification reactions were gel purified to homogeneity while all others were supplied as desalted preparations.

AmpX Amplification Reactions

DNA was amplified in 60 μL reactions containing 16 pmol of each primer, 10 mM KCl, 10 mM $(NH_4)_2SO_4$, 20 mM Tris-HCl pH 8.8, 200 μM dNTP, 2 mM $MgSO_4$, 0.1% v/v Triton X-100. A 2 μL aliquot of template was added to each reaction, which was followed by a denaturation cycle of 94° C. for 30 seconds and then equilibration to 55-60° C. for five minutes. Amplification was initiated by the addition of 4 U of Bst DNA polymerase (New England Biolabs) and the reactions were isothermally maintained at 60° C. for 2.5-3 hours.

Nucleic Acid Electrophoresis and Hybridisation

Amplified products were electrophoresed through 2% v/v agarose gels in TAE or TBE buffer (12) and visualized by ethidium bromide staining. Prior to blotting, nucleic acids were denatured in 0.5 M NaOH, 1.5 M NaCl for 30 minutes, followed by neutralization in 1 M Tris-HCl pH 8.0, 1.5 M NaCl for 30 minutes. Nucleic acids were then capillary transferred to Hybond-$N^+$ membrane (Amersham) according to the manufacturer's protocol. Oligonucleotide probes were 3' labeled with DIG-ddUTP using terminal transferase (Boehringer Mannheim).

Membranes were prehybridized in 5-10 ml of RapidHyb buffer (Amersham) at 42° C. for 30 minutes. The DIG-labeled oligonucleotides were then added to the hybridization buffer and hybridization at 42° C. overnight. The blots were washed and developed using CDP-Star (Boehringer Mannheim) as per the manufacturer's instructions.

Cloning and Sequence Analysis

Products of the amplification reactions were purified through Wizard PCR DNA purification columns (Promega) prior to cloning. The purified products were then ligated directly into the pGEM-T vector (Promega) at 16° C. for 3 hours, followed by electroporation into E. coli DH5α (13). Inserts were sequenced using dye termination chemistry and an Applied Biosystems 373A DNA sequencer.

EXAMPLE 2

AmpX Analysis—Results

AmpX Amplification from a Synthetic ssDNA Molecule

Figure 5A:
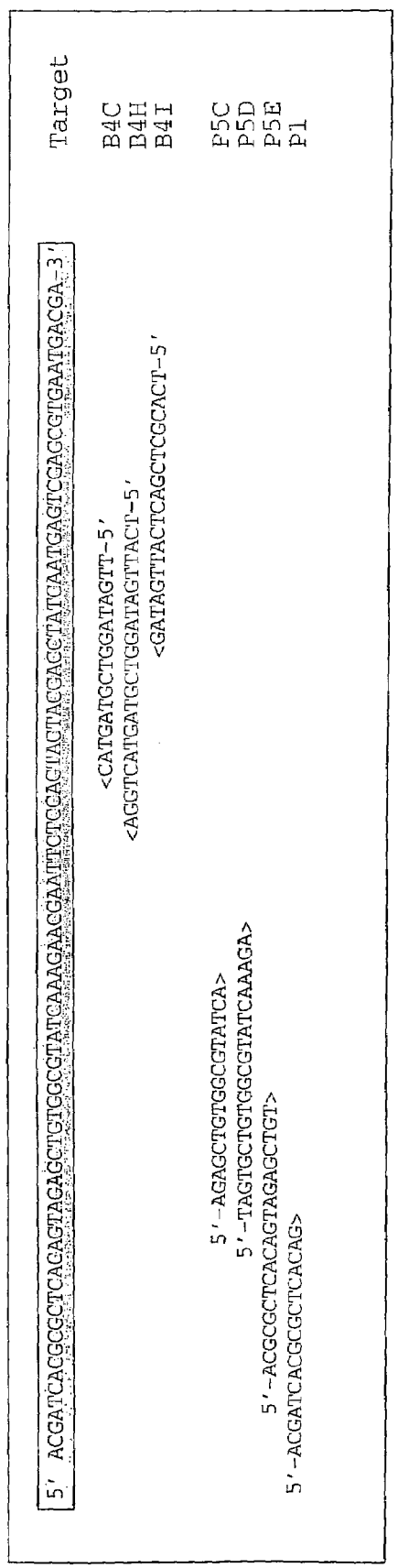
FIG. 5 is a photographic representation of isothermal amplification from a synthetic target molecule. Panel A is a diagrammatic illustration of the synthetic target molecule and primers used in the amplification reaction (<400>1-<400>8). Various combinations of these primers were used in isothermal amplification reactions. Following amplification 10 μL of products from each reaction were loaded onto a 2% w/v agarose gel alongside a 100 bp ladder (lane M), electrophoresed and visualized by ethidium bromide staining (Panel B). Reactions included a control using primers B4C/P5C to which no synthetic target was added (lane C), as well as reactions using primers P1/B4C (lane 1), P5C/B4C (lane 2), P5C/B4 (lane 3), P5C/B4I (lane 4), P4D/B4C (lane 5), P5D/B4I (lane 6) and P5E/B4I (lane 7).

A synthetic 90 mer oligonucleotide of random sequence was synthesized and used as a template in initial amplification reactions (FIG. 5A). A variety of smaller primers were also synthesized, based on the sequence of the template molecule. These were designed such that they varied in size, orientation and position with respect to the template molecule (FIG. 5A).

Figure 5B:
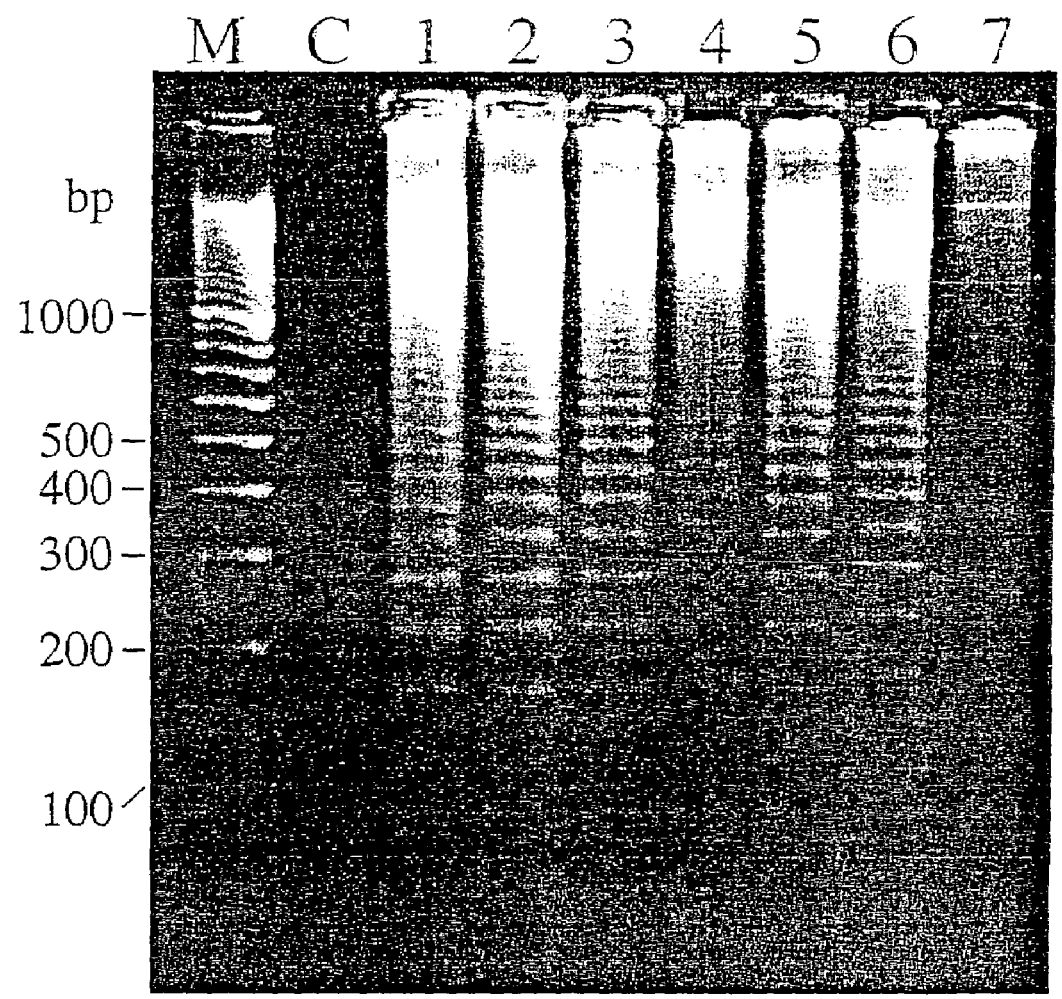

Various combinations of opposing primers were used in amplification reactions. Typically, 1 pmol of template was mixed with 16 pmol of each primer. Following denaturation and equilibration to 60° C., the reactions were initiated by the addition of the strand-displacing, exonuclease minus Bst DNA polymerase. The reactions were then incubated at 60° C. for 3 hrs before products were examined by agarose gel electrophoresis (FIG. 5B).

A population of products was produced from each of these reactions which had characteristic banding patterns, regardless of the primer combinations tested. The sizes of these products ranged from less than 100 nucleotides, to molecules that were so large that they remained in the wells following electrophoresis. Each of the products from a single amplification reaction appeared to differ in size from one another by a standard unit length. This unit length varied between different primer combinations utilized in the reactions. The level of DNA amplification also varied between different primer combinations, but in general, spectrophotometric assays indicated that the reactions were able to synthesize between 10 and 40 µg of products during a 3 hour reaction.

Furthermore, this isothermal amplification which appeared to produce a series of multimeric products, was not limited to just this one particular template sequence. A further six template sequences and their corresponding primer sets also yielded amplification products.

Analysis of the AmpX Amplification Products

The products from four separate amplification reactions, using different primer combinations, were analysed to determine their molecular composition. Initially the entire population of amplification products was analysed by digestion with four separate restriction enzymes, which had cleavage sites distributed across the template molecule. A more detailed analysis of particular reaction products was achieved by cloning and partially sequencing.

In general, amplification products from reactions where primers were situated away from the ends of the template molecule consisted of tandem repeats of a region of the template molecule which spanned from one primer binding site to the next. However, several repeats also included template sequence flanking the primer binding sites. In rare cases, the amplification products consisted of tandem repeats of a region of the template molecule as described above but including deletions. Occasionally, sequence deletions vary from one repeat unit to the next. Examples of some of the amplified regions are outlined below.

The majority of products from the amplification reaction using primers P5C and B4C were digested to low molecular weight products with AluI and EcoRI but not Sau3AI or TaqI (FIG. 6A(i)). This indicates that the amplified region consisted of tandem repeats of a region of the template molecule which included the primer binding regions plus their intervening sequence. Sequence analysis generally agreed with this notion, however, the amplified region was shown to include two additional nucleotides flanking the primer P5C binding site and one nucleotide from the 5' end of primer B4C was consistently absent in each of the repeat units (FIG. 6A(ii)). Interestingly, not all products from this reaction were digested with AluI or EcoRI even though digestions were performed using high restriction enzyme concentrations. This suggests that either point mutations or variations of other amplified regions were also present in some of the amplification products.

Similar results were observed when products were amplified from the template molecule using primers P5E and B4I, which were located closer to the 5' and 3' ends of the template molecule, respectively. The majority of products from this reaction were digested with AluI, EcoRI and TaqI and a significant amount of products were also digested with Sau3AI (FIG. 6B(i)). Sequencing analysis again indicated that the products consisted of tandem repeats of a region of the template molecule not only spanning from one primer binding site to the next but also included 6 and 7 nucleotides of sequence flanking the P5E and B4I primer binding sites, respectively. Interestingly, the cloned product from this reaction had point mutations in the regions flanking the primer binding site for P5E which would render this sequence insensitive to Sau3AI digestion. Hence, the restriction profile and sequence analysis suggests that the reaction products consist of a mixed population of molecules, the majority of which are arranged as tandem repeats of the entire template, and some of which have point mutations in the Sau3AI site.

Figure 6C:
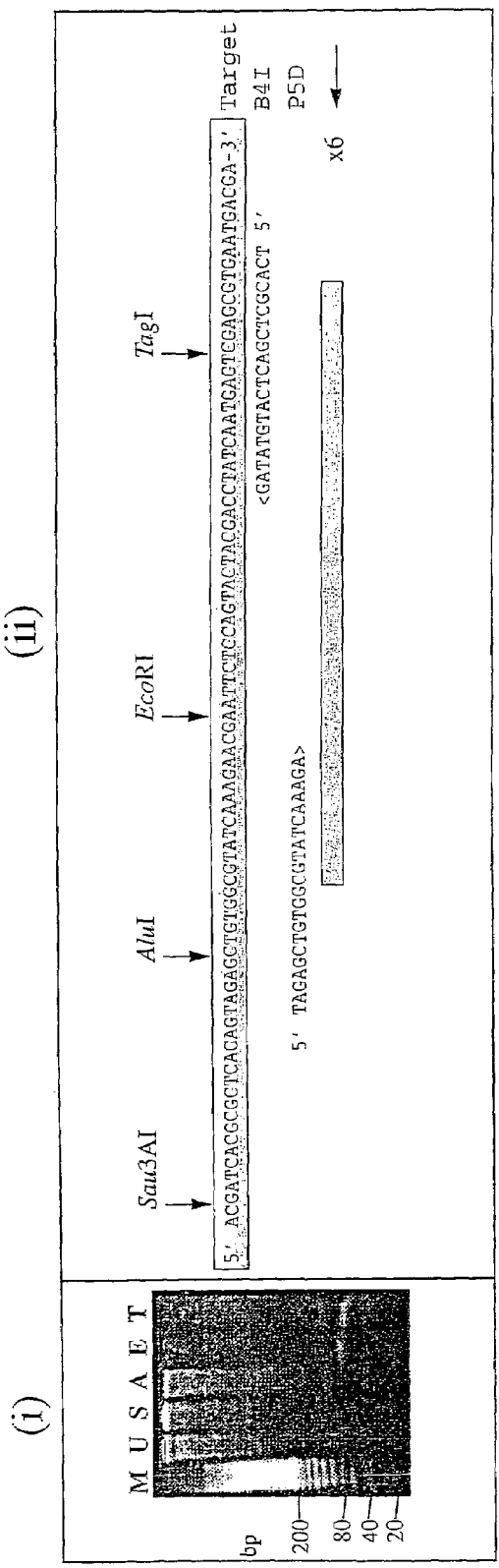
FIG. 6 is a photographic representation of restriction digest and sequence analysis of amplification products. Products for four separate amplification reactions using primers B4C/P5C (Panel A), B4I/P5E (Panel B), B4I/P5D (Panel C) and B4C/P1 (Panel D) were analaysed by restriction digestion and sequence analysis. An aliquot of each reaction was digested separately with Sau3A1 (lane S), AluI (lane A), EcoRI (lane E) and Taql (lane T) and electrophoresed through 2% w/v agarose gel alongside a 20 bp ladder (lane M) and an undigested control (lane U). Products were visualized by ethidium bromide staining (Column (i)). A reaction product for each amplification was also cloned and partially sequenced. Arrow next to the sequence representations indicate the direction of the sequence read from the clone. Numbers to the left of each molecule indicate the number of consecutive repeats of each molecule found. Lettering within the diagrammatic representations indicates mutations found in the repeat molecules. Spaces in individual repeat units indicates deletion present.

Products from the amplification reaction using primers B4I and P5D were digested only with EcoRI and TaqI, but not with Sau3AI or AluI (FIG. 6C(i)). This was unexpected as the AluI site is located within the sequence of primer P5D. Sequence analysis indicated that the products from this reaction contained tandem repeats of a region which included the B4I primer binding site and the intervening sequence of the template molecule between P5D and B4I but included only the last 11 nucleotides of the primer P5D (FIG. 6C(ii)). The AluI site is within the deleted region of P5D, thus explaining the inability of AluI to cleave the reaction products.

Figure 6D:
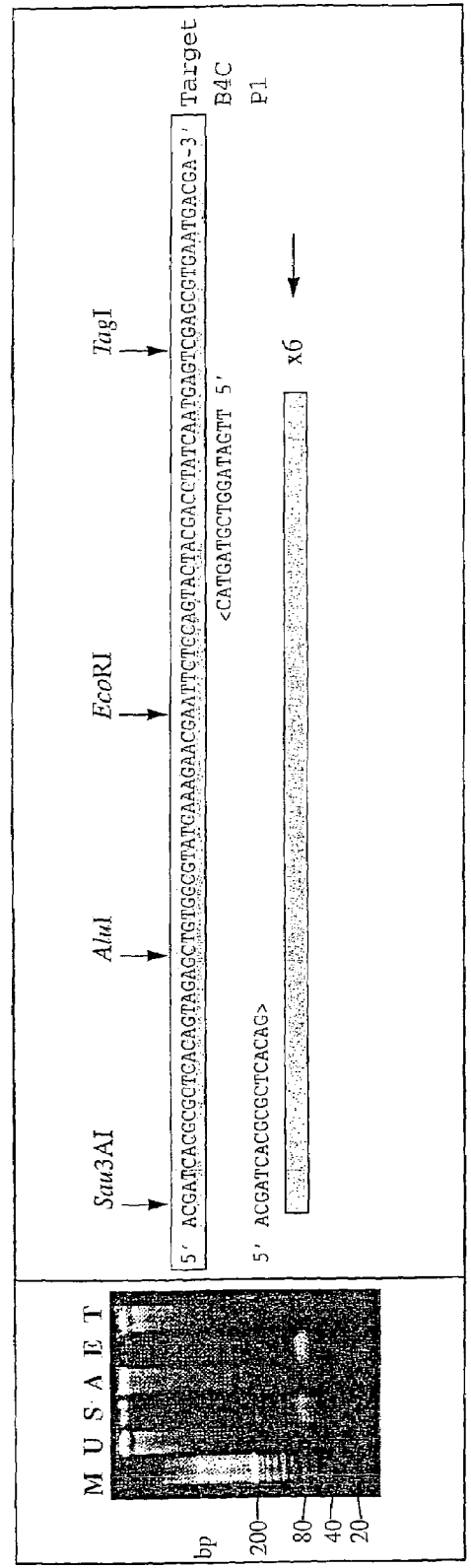

The majority of the products amplified from the template molecule with primers B4C and P1 digested with Sau3AI and EcoRI but not with AluI or TaqI (FIG. 6D(i)). This would suggest that the majority of the reaction products did not have a region of the intervening sequence between the two primer binding sites. Sequence analysis confirmed this, indicating that the amplified sequence included the primer binding sites of B4C and P1 plus the majority of the intervening sequence between the two primers but contained a 12 nucleotide deletion near the primer P1 binding site. The AluI site is within this deleted region thus explaining the inability of AluI to cleave the amplified products. The repeats also included one additional nucleotide flanking the primer binding site for B4C and had one nucleotide absent from the 5' end of the P1 primer binding site.

Products from other amplification reactions using different primer combinations were also cloned and sequenced, giving similar results to those examples outlined above.

Sensitivity of the AmpX Amplification Reaction

Figure 7:
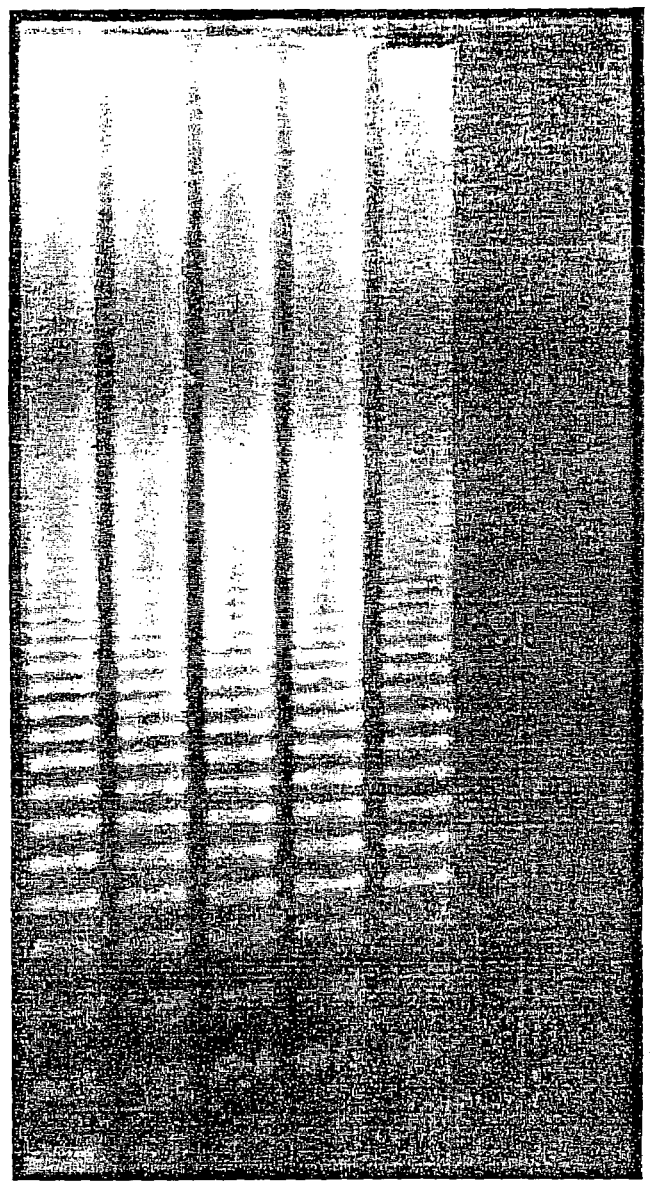
FIG. 7 is a photographic representation of sensitivity of amplification reaction. Serial dilutions of the synthetic target molecule were made and used as templates for the amplification reactions. Following amplification 10 μL of product from each reaction were electrophoresed through 2% w/v agarose gel and visualized by ethidium bromide staining.

The synthetic template oligonucleotide was diluted using 10 fold serial dilutions to determine the sensitivity limit of the amplification reaction. Using primers B4C and P5C in a 3 hour amplification the detection sensitivity of the reaction was approximately $10^{-4}$ picomoles of template. The detection sensitivity of other primer combinations and templates was similar, however, on several occasions the detection sensitivity increased to less than $10^{-8}$ picomoles of template (FIG. 7). This indicates the need for at least $1 \times 10^8$ copies of the template to initiate the reaction. Longer incubations generally did not increase the detection sensitivity of the assay. Amplification of 30 µg of product from $1 \times 10^{-4}$ pmol of template represents a potential $1 \times 10^7$ fold amplification.

AmpX Detection of the Mini-Transposon Tn10 Derivative in *E. coli*

Figure 8A:
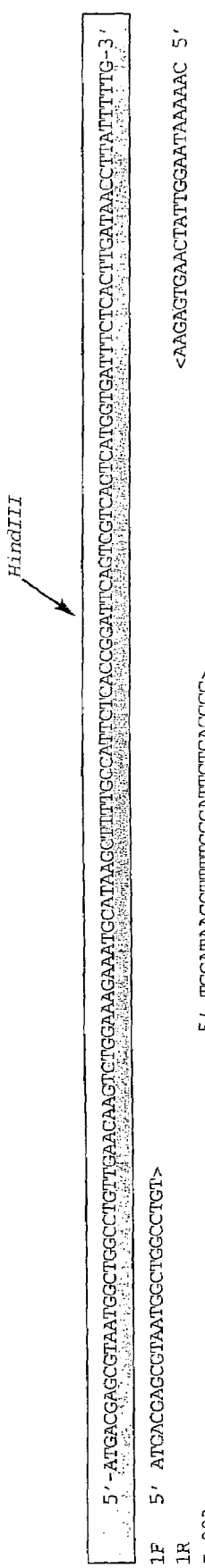
FIG. 8 is a photographic representation of the detection of mini-transposon containing *E. coli*. Primers designed to amplify a 120 bp region of the KanR mini-transposon (<400>9) are illustrated (Panel A), together with the oligonucleotide, In903 (<400>11), used as an internal hybridization probe. The primers 1F (<400>10) and 1R (<400>12) were used in reactions to amplify the mini-transposon sequence from various amounts of *E. coli* PNG801 genomic DNA, carrying this particular mini-transposson. Amplification reactions were also carried out on various amounts of *E. coli* DH5α genomic DNA, as a negative control following amplification 1 μL of product was digested with HindIII (lane H) and electrophoresed through a 2% w/v agarose gel alongside an undigested control (lane U) and molecular weight markers (lane M). Control reactions were also included to which no template was added.

In order to demonstrate the potential ability of the AmpX reaction to amplify a known sequence of interest from a genomic template, amplification reactions were performed to detect the presence of *E. coli* genomes that contained a particular mini-transposon sequence. Primers 1F and 1R were designed to amplify a sequence which included a 120 base pair region of the mini-transposon Tn10 derivative (FIG. 8A). This region also included a HindIII site. An additional primer, In903, located between 1F and 1R was also synthesized to use as a probe for detecting the presence of some of the intervening sequence within the reaction products (FIG. 8A).

Duplicate reactions were set up using various amounts of the genomic DNA from both Tn10 positive and negative *E. coli* strains. Following denaturation and Bst polymerase addition, standard AmpX amplification reactions were carried out using isothermal conditions at 60° C. for 2.5 hours. Following amplification 1 µL of each reaction was digested with HindIII (FIG. 8A).

Figure 8B:
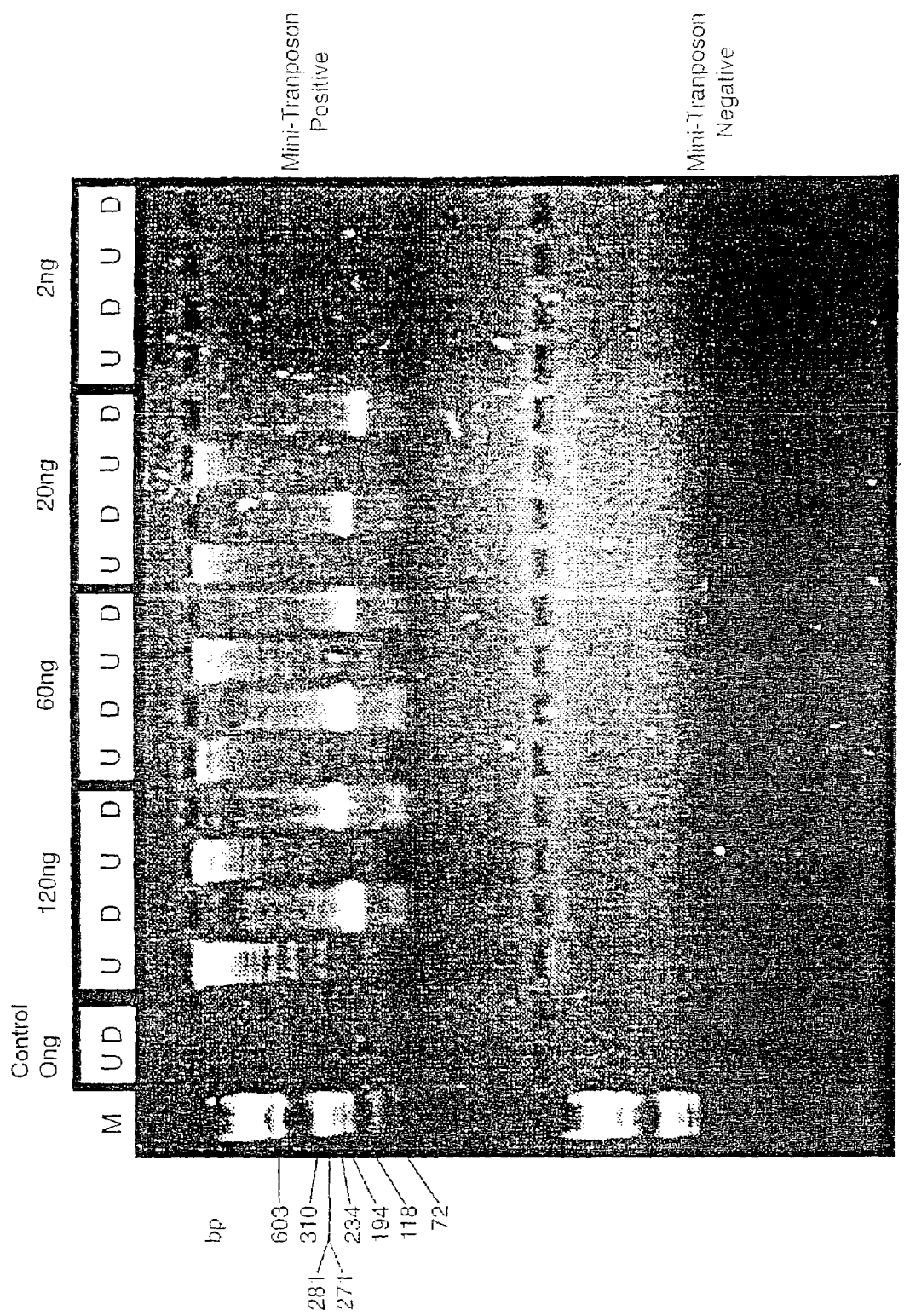

Undigested and HindIII cleaved products were electrophoresed side by side through a 2% agarose gel and visualized by staining with ethidium bromide (FIG. 8B). No products were observed in control reactions, to which no template was added. Similarly, no products were amplified in any reactions to which *E. coli* DH5α genomic DNA was added. However, when 20 ng or more of the *E. coli* PNG801 genomic DNA was added to the reaction, amplification occurred.

The population of products amplified in each of the reactions were similar to those observed using the oligonucleotide template. They ranged in size from just over 100 base pairs to extremely large molecules. Each of the products from a single amplification appeared to differ in size from one another by a standard unit length. However, in this example the unit length varied quite dramatically from reaction to reaction even though the primer combination remained unchanged. This was thought to possibly represent variations in the initiation events of the reaction that led to this amplification occurring. Digestion of the reaction products with HindIII indicated that the majority of the products from each of the reactions contain a uniform repeat size. Furthermore, the labelled internal probe, In903, was able to hybridise with all reaction products verifying the presence of that region of the intervening sequence in the reaction products.

Sequence analysis of products from three separate amplification reactions revealed different sets of tandem repeat units within each of the populations, as expected. Each contained both primer binding sites and the corresponding intervening sequence but differed in the length of sequence flanking each of the primer binding sites. The length of this additional sequence varied between none to 77 nucleotides. The sequence of the repeat unit did not appear to change between individual repeats in the molecules sequenced. In some experiments with the *E. coli* PNG801 genomic DNA template, where multiple reactions were performed using a single primer set and a single template concentration, several of the identical reactions failed to amplify. This and the evidence of different amplified regions tends to suggest that specific initiation events need to take place for the reactions to proceed.

EXAMPLE 3

Padlock Circularisation for Rolling Circle Amplification

Tagged Spacer Protocol

Figure 9:
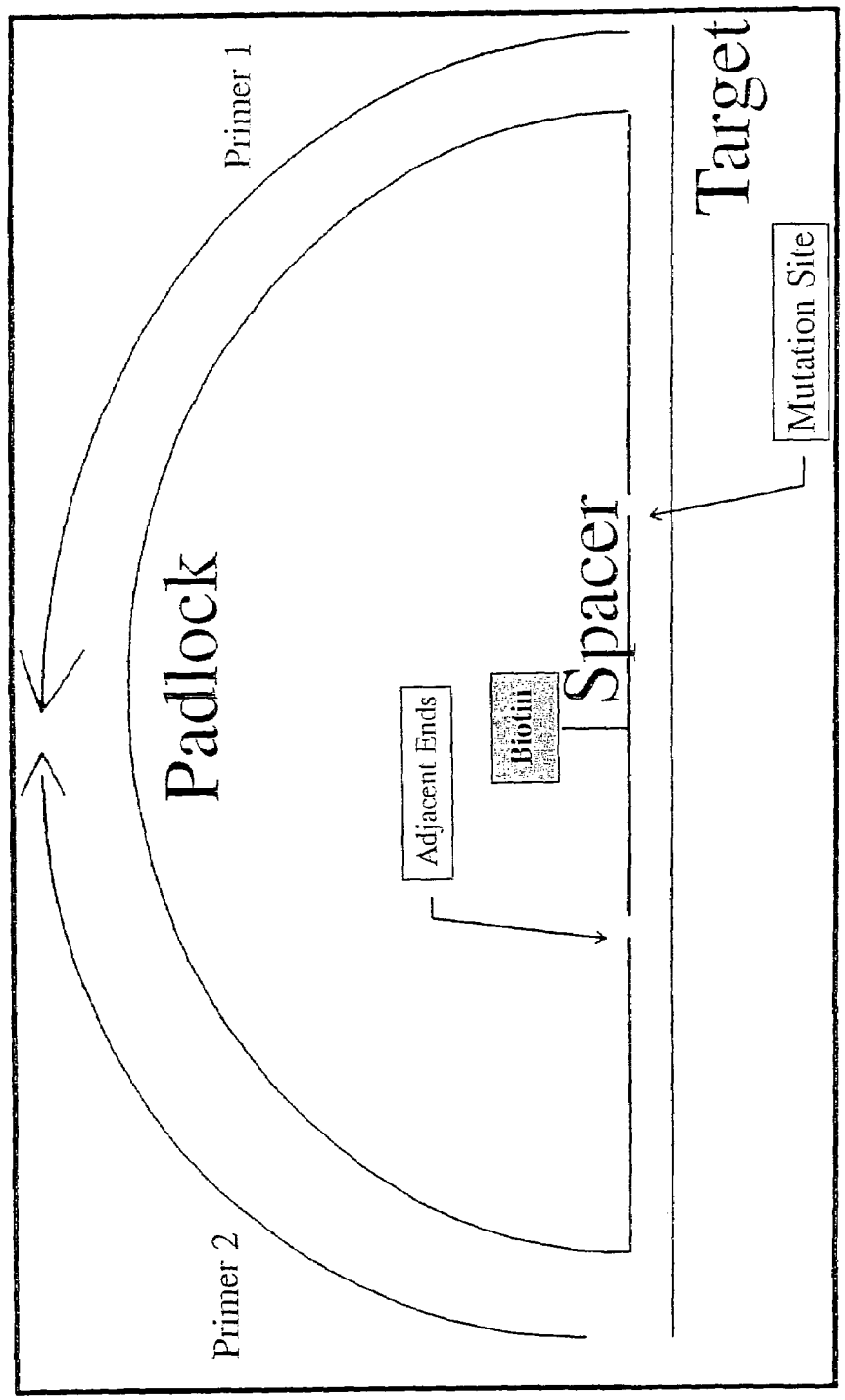
FIG. 9 is a schematic diagram of padlock hybridisation and circularisation.

This procedure outlines the general method for generation of closed circular probes utilizing tagged spacer oligonucleotides complementary to the target of interest. The experimental design for the padlock probes, target sequences and other essential components is illustrated in FIG. 9.

A 50 µL reaction volume contained 1 pmol of padlock oligonucleotide, 1 pmol of spacer oligonucleotide and 1 pmol of synthetic oligonucleotide target in ligation buffer (20 mM Tris-HCl, pH 8.3, 25 mM KCl, 10 mM MgCl$_2$, 0.5 mM NAD, 0.01% v/v Triton X-100). The reaction was initially heated to 94° C. for 3 minutes. Once the tube had reached 94° C., 1 µL of Ampligase (5 U/µL; Epicentre Technologies) was added. The reaction was then cooled to 60° C. and incubated for 1 hour to allow the ligation to take place.

Gap-Fill Protocol

This procedure outlines the protocol for the generation of closed circular probes utilizing tagged nucleotides in a gap-fill reaction. The experimental design of this approach is similar to that illustrated in FIG. 9, however, the tagged spacer is replaced by a gap-fill reaction with tagged nucleotides.

A 50 µL reaction volume contained 1 pmol of padlock oligonucleotide, 1 pmol of synthetic oligonucleotide target, 15 pmol of biotin-14-dATP and 15 pmol of each dGTP, dTTP and dCTP in ligation/gap-fill buffer (50 mM N-(2-hydroxyethyl) piperazine-N-(3-propanesulfonic acid) [EPPS], 180 mM K$^+$ (KOH added to adjust pH to 7.8 and KCl added for final K$^+$ concentration), 10 mM MgCl$_2$, 10 mM NH$_4$Cl, 100 µm NAD$^+$, 100 µg bovine serum albumin (BSA). The reaction was initially heated to 94° C. for 3 minutes. Once the tube had reached 94° C., 1 µL of enzyme mixture (Ampligase 5 U/µL; Epicentre Technologies & Taq polymerase 1 U/µL; Perkin Elmer) was added. The reaction was then cooled to 60° C. and incubated for 1 hour to allow the ligation and gap-filling reactions to take place.

In both circularisation procedures the amount of molecular tag should not exceed the maximum binding capacity of the affinity substrate medium used in the purification procedure.

EXAMPLE 4

Padlock Purification for AmpX Minimized Rolling Circle Amplification

Preparation of Beads

Presently streptavidin coated superparamagnetic beads (Dynal) are used for most purification reactions. These beads are supplied in a buffer containing preservatives and are therefore washed prior to use. A 125 µL aliquot of the initial bead mixture is needed for each five 50 µL ligation reactions.

Beads were aliquoted into 1.5 ml microfuge tubes. The beads were isolated on a magnetic platform, the supernatant removed and the beads then resuspended in 125 µL of 2×BW buffer (10 mM Tris-HCl pH 7.5, 1 mM EDTA, 2M NaCl). This procedure was repeated three additional times before finally resuspending the beads in 250 µL of 2×BW buffer.

Capture of Closed Circle Molecules

50 µL of the washed beads was mixed with 50 µL of ligation reaction and incubated at room temperature for 30 minutes, mixing periodically to keep the beads in solution. The beads and consequently attached tagged molecules were then captured using a magnetic platform and the liquid removed. Beads were then resuspended in 100 µL of 1×BW buffer (5 mM Tris-HCl pH 7.5, 0.5 mM EDTA, 1M NaCl). This wash procedure was the repeated again once with 1×BW buffer, three times with 0.1M NaOH (5 minutes each) to remove any hybridized molecules and finally twice with TE to wash and neutralize the beads. The beads were then finally resuspended in 50 µL TE (10 mM Tris HCl pH 8.0, 1 mM EDTA).

EXAMPLE 5

RCA Amplification With or Without Circle Enrichment

A 60 µL reaction contained 10 pmoles of each amplification primer, 167 µM dNTPs, and 1 µL of ligation reaction (unpurified or purified) in 20 mM Tris-HCl pH 8.8 (25° C.), 10M KCl, 10 mM $(NH_4)_2SO_4$, 2 mM $MgSO_4$, 0.1% v/v Triton X-100. The reactions were heated at 94° C. for 3 minutes before being cooled to the desired amplification temperature (50-70° C.) for 5 minutes. 0.5 µL of Bst DNA pol. (8 U/µL; NEB) was added to each of the reactions and the tubes were incubated at the desired amplification temperature for 1½-2 hours.

Time can be increased of decreased depending on the amount of circle present and the efficiency of the particular amplification reaction.

EXAMPLE 6

Advantages of Enriching Tagged Circular Molecules for Rolling Circle Amplification When rolling circle amplification (RCA) reactions are performed using crude ligation reactions, two standard types of banding are typically evident (FIG. 10). When template is present and in sufficient concentration a typical RCA banding pattern is seen as a ladder of DNA molecules that differ in size from one another by a standard unit length (FIG. 10 unpurified and purified +ve lanes). Accordingly, this unit length corresponds to the size of the circular molecule utilized as the target in the RCA reactions. When no template or insufficient template is present in the RCA reactions a different type of banding pattern is visualized. Again the products are arranged as a ladder of DNA molecules that differ in size from one another by a standard unit length but this unit length does not correspond to the size of the expected circular molecule. Instead the size of the repeat is typically the same size as the intervening region between the two primers (FIG. 10 unpurified –ve lane). This background reaction has been termed "Amp X". It has also been demonstrated that this background reaction is due to remaining uncircularized padlock probe that remains in the reaction following ligation. Utilizing tagged spacer molecules in closed circular probe generating reactions with padlock oligonucleotides it is possible to incorporate the tagged molecules into the closed circular probes. These tagged molecules can then be purified using an affinity between the molecular tag and the substrate therefor. Through subsequent washing steps under both non-denaturing and denaturing conditions templates for the RCA reactions which are free from this Amp X background, can be generated (FIG. 10 purified –ve lane).

EXAMPLE 7

Improved RCA from Genomic Templates

Figure 12:
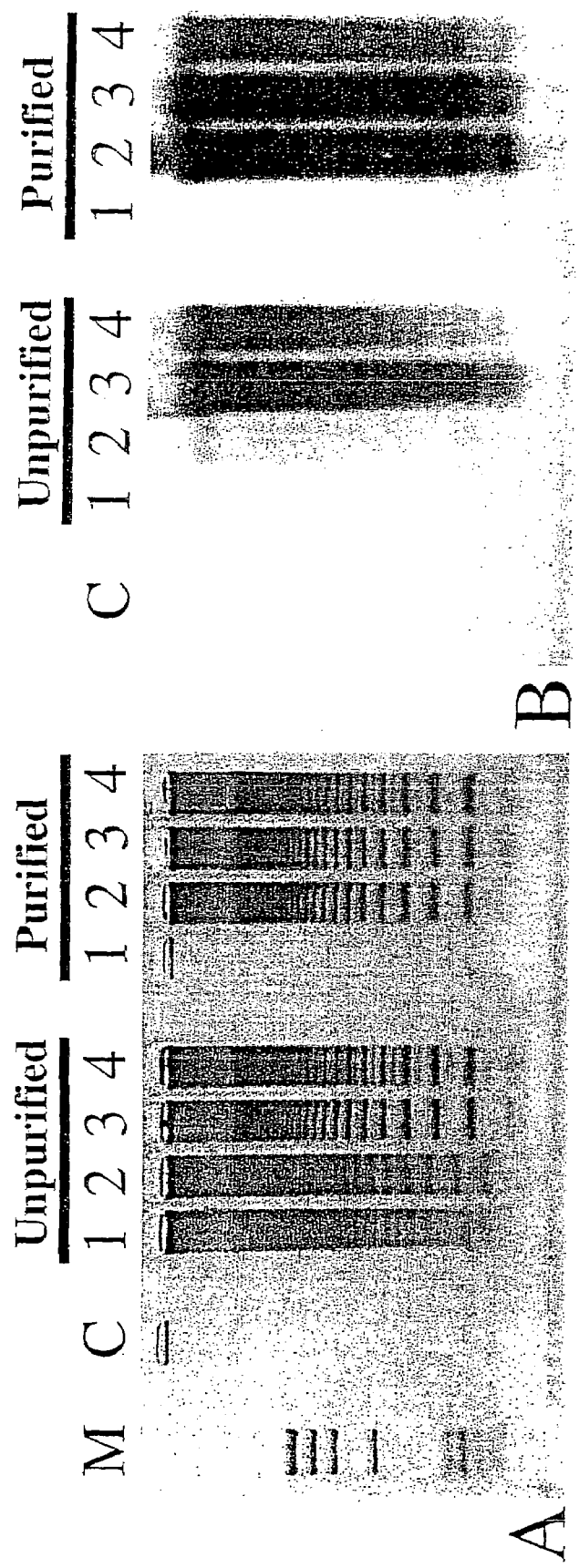
FIG. 12 is a photographic representation of the comparison of unpurified and purified templates for RCA reactions.

Utilizing the closed circular probe generation (tagged spacer) and purification protocols, the versatility of the new RCA procedure was tested using sequences shown in FIG. 11. Four different ligation reactions were setup in duplicate. The negative control reaction (FIG. 12 lane 1) contained Padlock FV2 and LigW but did not contain any template nor was any ligase added to the reaction in subsequent steps. Homozygous wildtype human gDNA (770 ng) was used as a template in ligation reaction with Padlock FV2 and LigW (FIG. 12 lane 2). Two other positive control ligation reactions was also setup; a wildtype control reaction (FIG. 12 lane 3) which contained Padlock FV2, LigW and used the wildtype target oligonucleotide (1 pmol) as the template and a mutant control reaction (FIG. 12 lane 4) which contained Padlock FV2, LigM and used the mutant target oligonucleotide (1 pmol) as the template. All reactions were heated to 94° C. prior to the addition of 1 µL of Ampligase. The reactions were then cooled to 60° C. and incubated for 1 hour to allow ligation to take place. Following ligation one set of reactions was purified using the outlined protocol and finally resuspended in the same volume as the untreated reactions.

The unpurified and purified ligation reactions were then used as templates for RCA, again using primers FV3 and FV4 in amplifications at 60° C. for 1 hour 40 minutes. Only 1 µL of each ligation was added to RCA reaction which equates to the equivalent of 15.4 ng of human gDNA or 20 fmol of oligonucleotides being used as templates for the respective ligation reactions. An RCA reaction was also done without the addition of template to determine whether any background present was due to the amplification primers FV3 and FV4 (FIG. 12 lane C). A 10 µL aliquot of each reaction was electrophoresed through 2% agarose in TBE buffer, alongside φX174 HaeIII digested DNA marker (FIG. 12 lane M) and visualized by ethidium bromide staining (FIG. 12; Panel A). The gel was then Southern blotted to nylon membrane and hybridized with a labeled LigW probe at 45° C. overnight to demonstrate which amplified DNA species contained the sequence of the intervening region between the two ends of the padlock probe (FIG. 12, Panel B).

Following ethidium bromide staining no background banding was present in the amplification reaction to which no template was added (FIG. 12 Panel A; lane C). When the unpurified templates were amplified, multimeric banding patterns were visualized in all lanes. The majority of the bands in the oligonucleotide controls appeared to be the correct RCA products with the standard unit length between the products corresponding to the correct size of the expected circular molecules (FIG. 12 Panel A; unpurified lanes 3 & 4). However, banding patterns consistent with that of the Amp X reactions were present in the negative control reaction (FIG. 12. Panel A; unpurified lane 1) and a mixture of the Amp X and RCA banding patterns appeared to be present in the human gDNA sample (FIG. 12 Panel A; unpurified lane 2).

The purified ligation reactions in contrast gave a completely different set of results. Again the majority of the bands in the oligonucleotide controls appeared to be the correct RCA products with the standard unit length between the products corresponding to the correct size of the expected circular molecules (FIG. 12 Panel A; purified lanes 3 & 4). However, purification appeared to have removed the Amp X background from the negative control reaction (FIG. 12 Panel A; purified lane 1) and furthermore appeared to clean up the banding patterns present in the human gDNA reaction such that it appeared to be more consistent with the RCA products (FIG. 12 Panel A; purified lane 2) without the additional Amp X background. Probing these reactions with labeled LigW oligonucleotide further supported this evidence by indicating that all the DNA produced in the unpurified negative control reaction did not contain the correct sequence for the intervening region between the two ends of the padlock probe (FIG. 12 Panel B; unpurified lane 1). The probe results also indicated that while some of the amplified sequence from the human gDNA ligation, which was not purified prior to RCA, did contain the correct sequence of interest between the two ends of the padlock probe the majority of the DNA amplified did not contain this sequence (FIG. 12 Panel B; unpurified lane 2). In contrast, the majority of the DNA amplified from the purified human gDNA ligation appeared to contain the sequence with the correct intervening region.

EXAMPLE 8

Sensitivity of RCA Reaction

Figure 13:
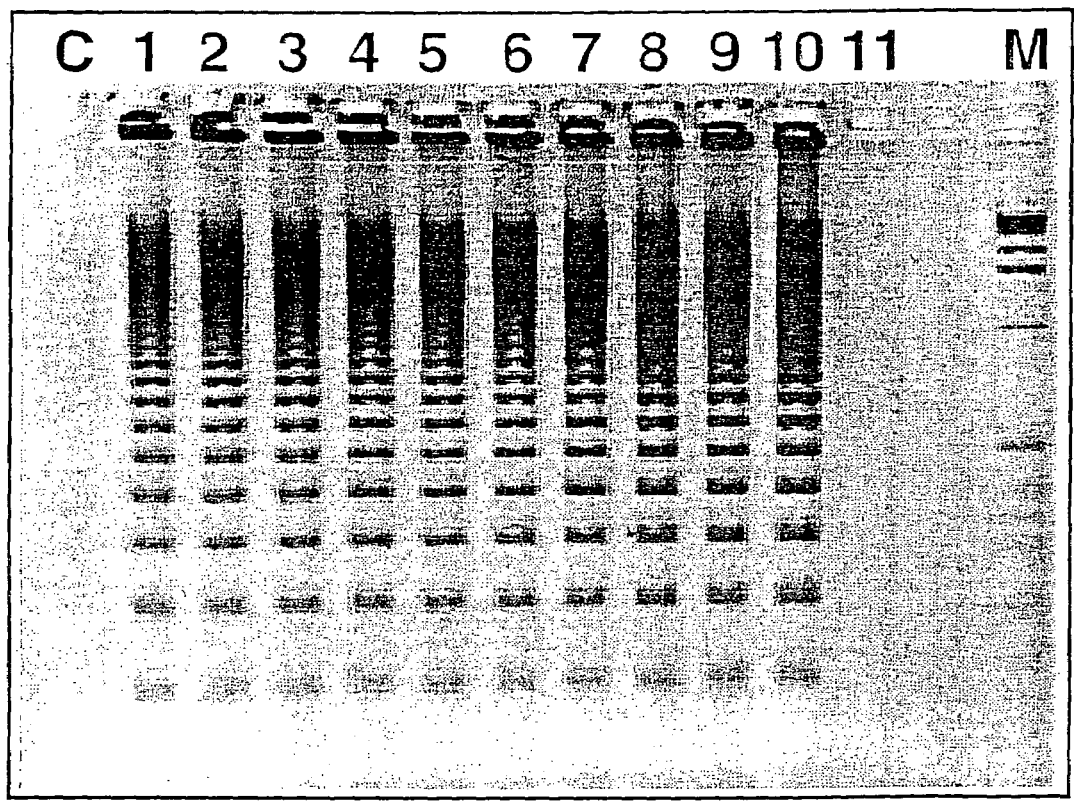
FIG. 13 is a photographic representation of the sensitivity of RCA from purified circles. Ten fold serial dilutions of purified circular molecules were used as templates for RCA reactions at 60° C. for 2.5 hours. The number of circles present in each reaction were estimated to be $8 \times 10^9$ (lane 1), $8 \times 10^8$ (lane 2), $8 \times 10^7$ (lane 3), $8 \times 10^6$ (lane 4), $8 \times 10^5$ (lane 5), $8 \times 10^4$ (lane 6), $8 \times 10^3$ (lane 7), $8 \times 10^2$ (lane 8), $8 \times 10^1$ (lane 9) 8 (lane 10), 0.8 (lane 11). In addition a negative control reaction was also included to ensure no primer artifacts were generated during the course of the reaction. A 10 µL aliquot of each of the amplified products was electrophoresed through 2% w/v agarose in TBE buffer, alongside DNA marker X (Roche; lane M) and visualised by ethidium bromide staining.

As outlined in Example 7 it was possible to detect a sequence of interest from as little as 15.4 ng of human gDNA using RCA reactions. The sensitivity of RCA has been further tested on purified circular molecules. Specifically, untagged circular molecules have been purified by excising the correct band from ligation reactions, using synthetic target molecules, run out on denaturing polyacrylamide gels. These circular molecules were extracted, purified and quantitated using UV spectrophotometric analysis. Dilutions of this purified material were then used as templates in RCA reactions (FIG. 13).

Figure 14:
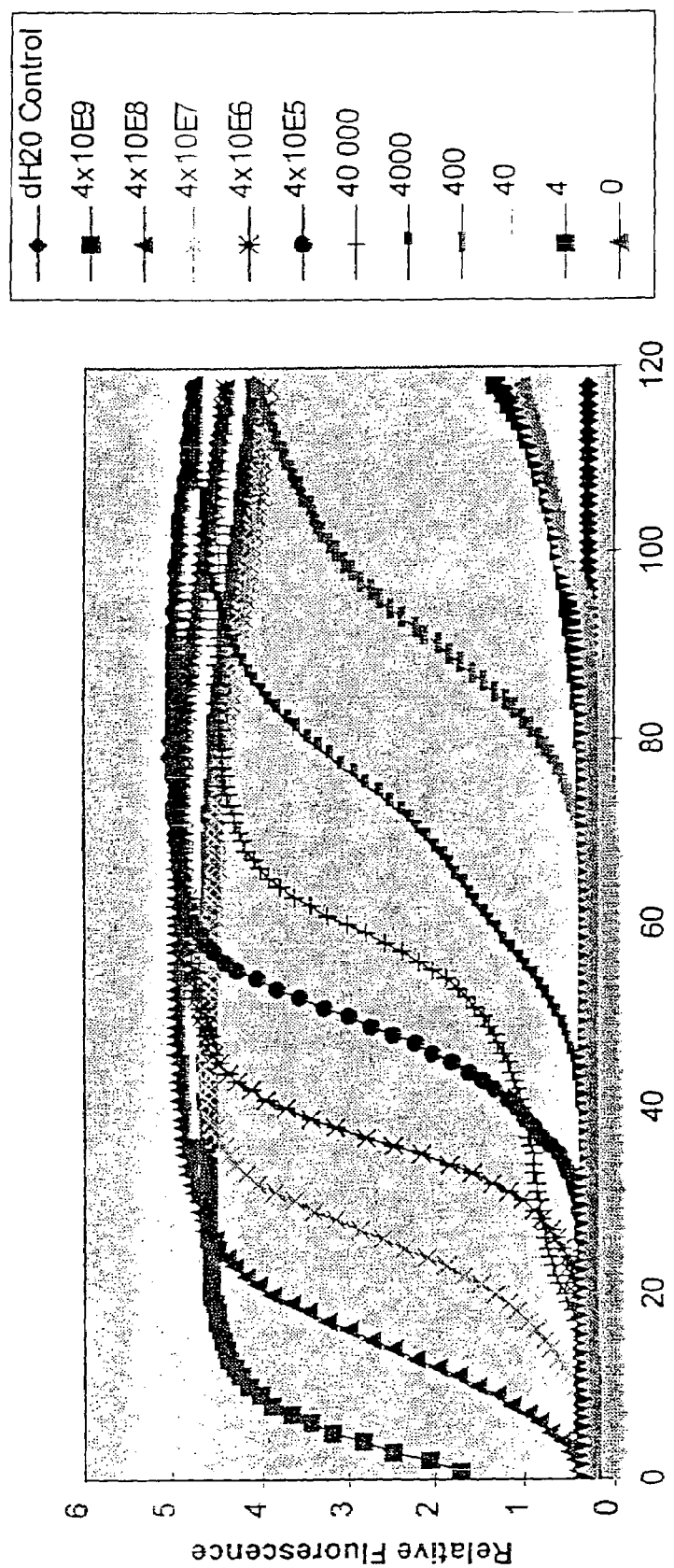
FIG. 14 is a graphical representation of real time visualisation of rolling circle amplification reactions.

As illustrated the reaction was able to detect fewer than 10 circular molecules present in the RCA reactions. Furthermore, if these reactions are slightly modified by the addition of 15 µg of bovine serum albumin and 1 µL of Sybr Green (1:1000 dilution; Molecular Probes) to the reaction buffer, the reactions can be followed using real time fluorescence measurements to estimate the amount of DNA generated (FIG. 14).

Figure 15:
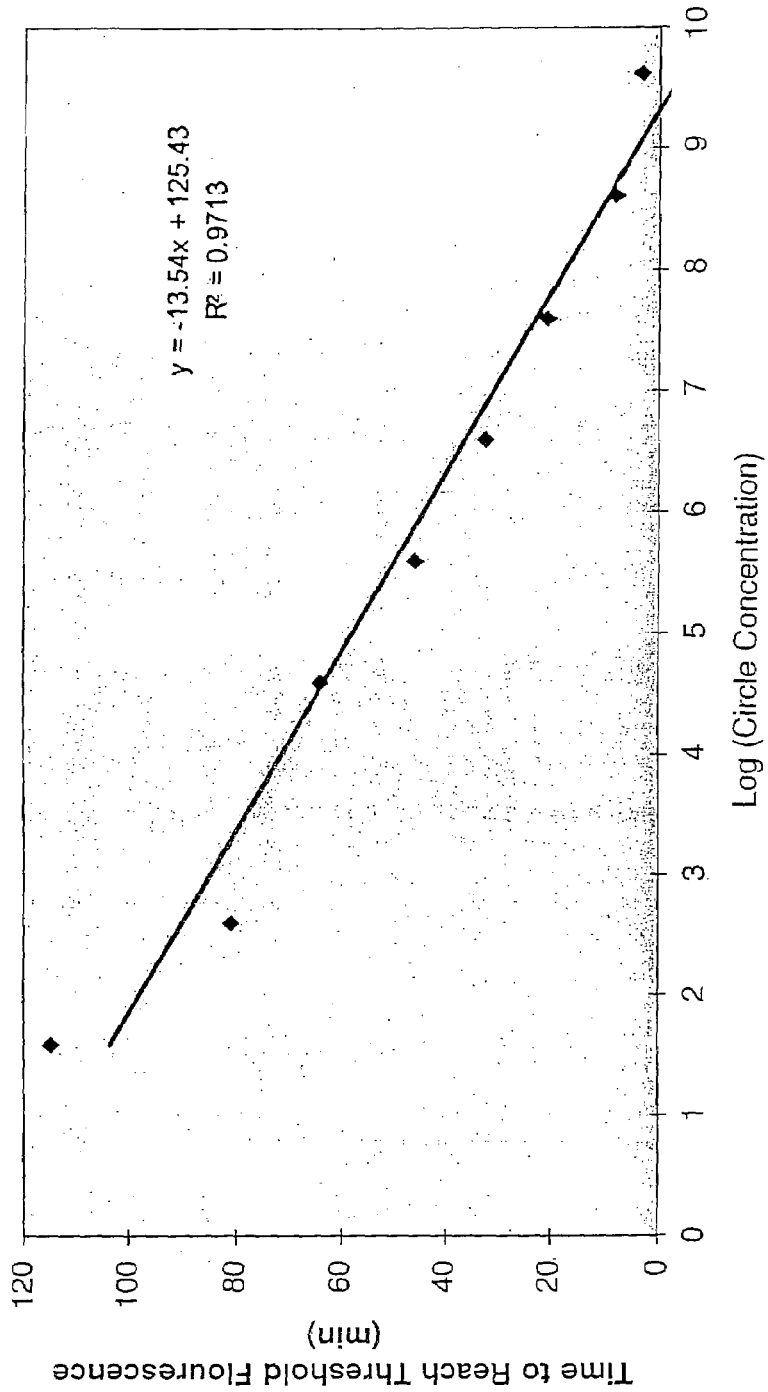
FIG. 15 is a graphical representation of the linear relationship between number of circles present and time to reach threshold fluorescence.

Using this data a threshold fluorescence level can be chosen and when the time taken for each sample to reach this threshold is plotted against the log of the amount of circular molecules present a linear relationship is observed (FIG. 15). Hence RCA reactions are quantitative and allow prediction of the number of circles added to an amplification reaction.

EXAMPLE 9

Specificity of RCA Reactions

Using the closed circular probe generation (tagged spacer) and purification protocols it has ben possible to demonstrate the specificity of RCA for detecting the correct sequence of interest. Using the oligonucleotide setup as outlined in FIG. 11 for the detection of the human factor V gene and genomic templates which either code for this gene (i.e. Human gDNA) or do not code for the gene (i.e. *Escherichia coli* gDNA) we are able to demonstrate that the closed circular probe generation only occurs when the DNA coding the gene of interest is present, and ligation reactions carried out under the conditions described.

Figure 16:
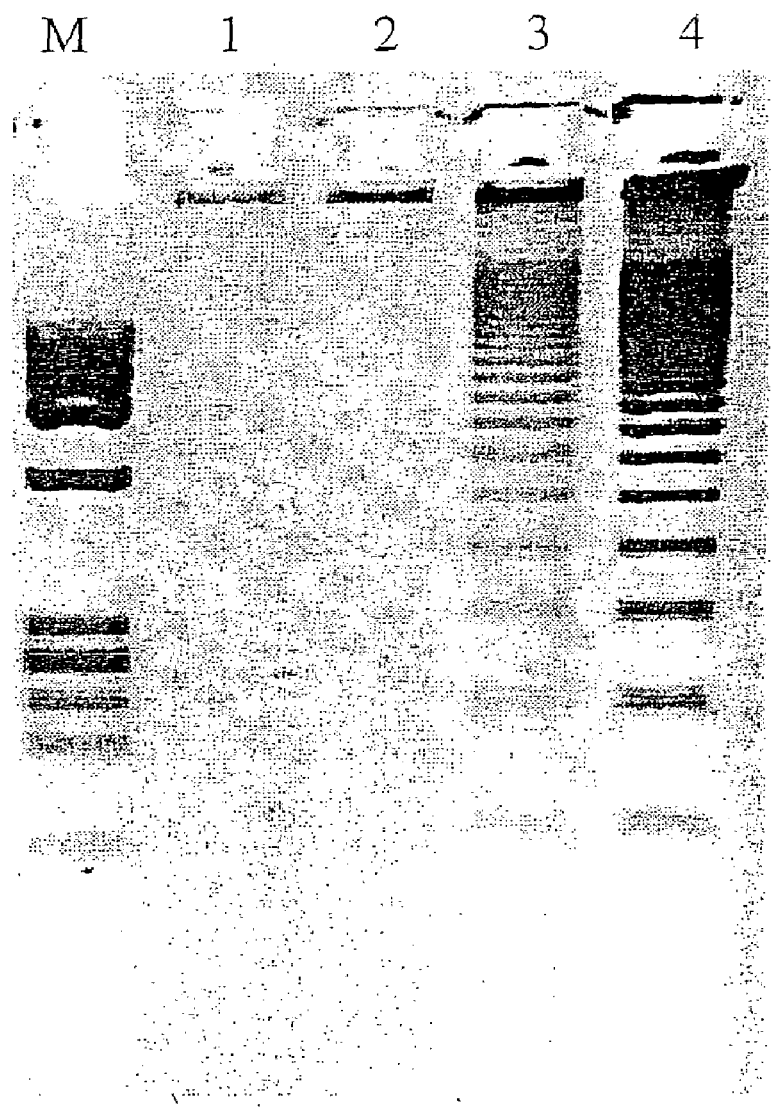
FIG. 16 is a photographic representation of the ability of RCA to specifically detect a gene of interest.

Four separate ligation reactions were set up, each containing the Padlock FV2 and LigW oligonucleotides. No template was added to the negative control reaction (FIG. 16 lane 1) nor was any ligase added to the reaction in subsequent steps. Purified *E. coli* gDNA (20 ng) was used as the negative gDNA substrate (FIG. 16 lane 2) in one reaction, while purified homozygous wildtype human gDNA (20 ng) was used as the positive gDNA substrate (FIG. 16 lane 3) in another reaction. In addition the wildtype target oligonucleotide (1 pmol) was used as positive control for circle generation (FIG. 16 lane 4). All reactions were heated to 94° C. prior to the addition of 1 µL of Ampligase. The reactions were then cooled to 60° C. and incubated for 1 hour to allow ligation to take place. Following ligation the reactions was purified using the outlined protocol and finally resuspended in the same volume as the untreated reactions.

Half the each of the purified ligation reactions were then used as templates for RCA, again using primers FV3 and FV4 in amplifications at 60° C. for 2 hours. This equates to the equivalent of 10 ng of *E. coli* gDNA, 10 ng of human gDNA or 0.5 pmol of oligonucleotide being used as templates for the respective ligation reactions. A 10 µL aliquot of each reaction was electrophoresed through 2% agarose in TBE buffer, alongside φX174 HaeIII digested DNA marker (FIG. 16 lane M) and visualized by ethidium bromide staining (FIG. 16).

It is clearly evident that RCA products are only produced from those reactions where it was possible to form the correct closed circular template molecule prior to RCA amplification.

EXAMPLE 10

Detecting Single Nucleotide Polymorphisms Using Closed Circle Enriched RCA

RCA is able to differentiate single nucleotide polymorphisms (SNPs) when they are incorporated into the closed circular probes. Wildtype and mutant circles were generated in ligation reactions using Padlock FV2 with either LigW and wildtype target oligonucleotide (1 pmol) for generating wildtype circles (W) or LigM and mutant target oligonucleotide (1 pmol) for generating mutant circles (M) (see FIGS. 11 and 17). A negative control reaction to which no template was added nor ligase added during subsequent steps was also included (C). Ligations were carried out according to the standard protocol at 60° C. for 1 hour and circles were then purified using the standard purification protocol.

Figure 17:
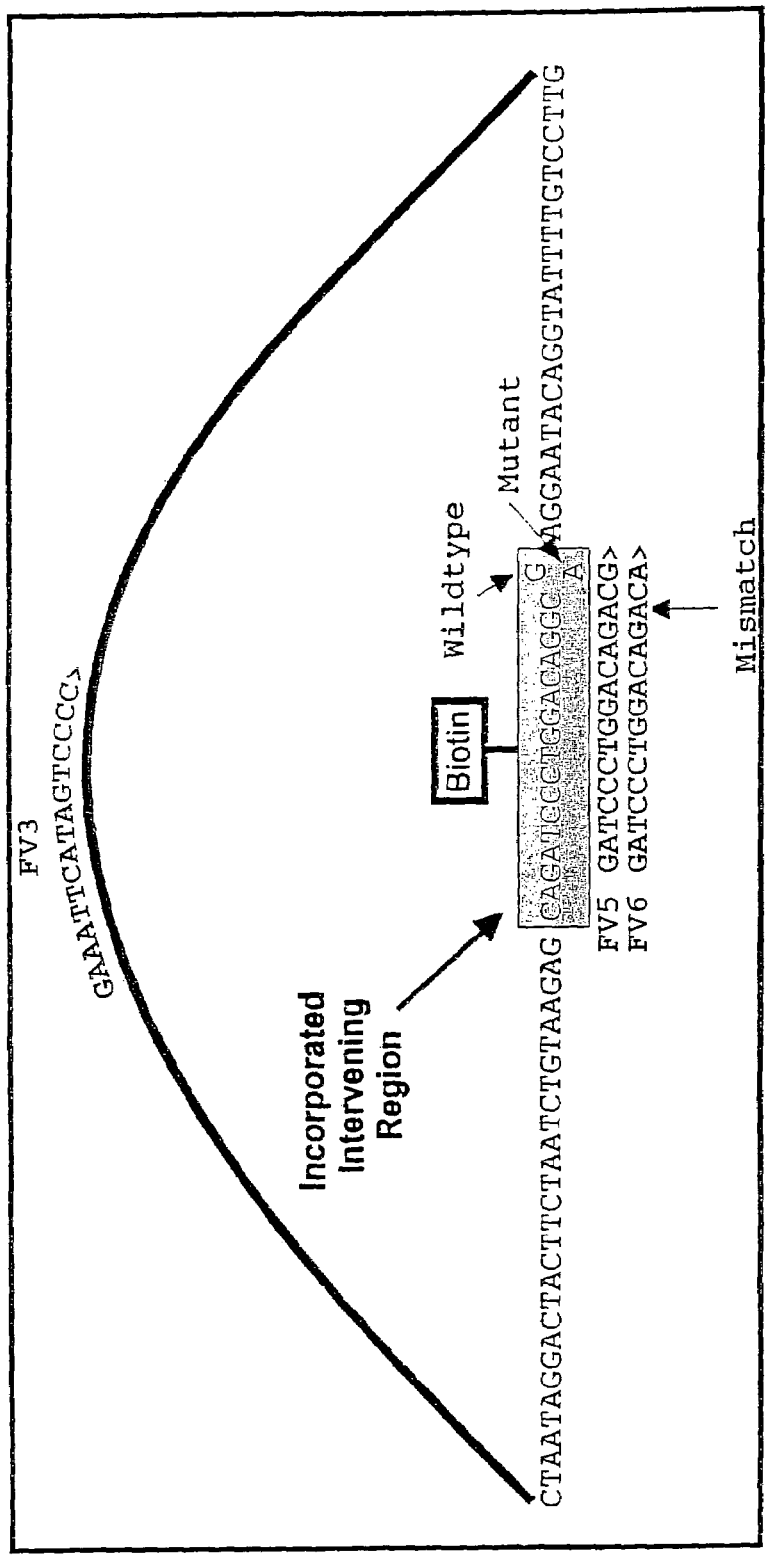
FIG. 17 is a schematic representation of the oligonucleotide design for SNP detection of factor V Leiden normal and mutant sequences (Wildtype sequence: <400>20; Mutant sequence: <400>21; FV5: <400>22; FV6: <400>23; FV3: <400>18).

For RCA reactions to differentiate between SNPs, the amplification primers require careful design. Generally one primer is designed to a region of the closed circular probe that represents the "backbone" of the padlock probe. The amplification specific primers, however must be designed with their 3' end adjacent to the mutation specific base. It is also thought that mutations in the oligonucleotide downstream to the last base on the 3' end of the primer will also help in differentiation during amplification. The primers chosen for SNP detection with respect to the factor V gene are illustrated in FIG. 17.

Figure 18:
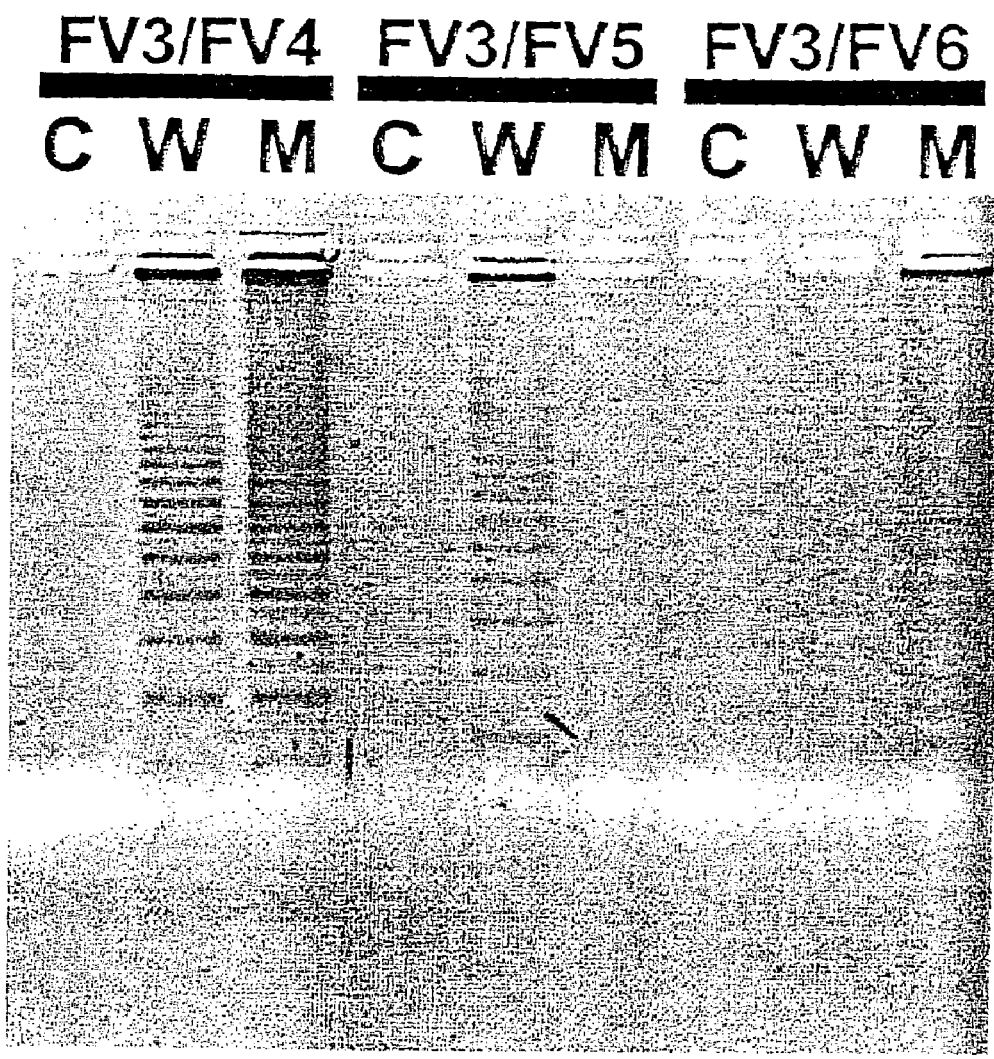
FIG. 18 is a photographic representation of the potential of RCA for SNP detection.

When standard RCA reactions were carried out at 63.5° C. for 1.5 hours using primers FV3 and FV4, electrophoresed through 2% w/v agarose in TBE buffer and visualized by ethidium bromide staining, it was possible to detect both wildtype and mutant circles (FIG. 18; FV3/FV4). However, when reactions were done using primers FV3 and FV5 only wildtype circles were amplified (FIG. 18; FV3/FV5). Similarly, when reactions were done using primers FV3 and FV6 only mutant circle were amplified (FIG. 18; FV3/FV6). No DNA was amplified in any of the negative control reactions. Hence, by using allele specific primer in conjunction with RCA we are able to identify SNPs.

EXAMPLE 11

Discrimination of *Chlamydia pneumoniae* and *trachomatis* Derived Sequences Using RCA SPA This example involves discriminating between synthetic DNA targets derived from *Chlamydia trachomatis* and *Chlamydia pneumoniae*:

1. The targets were 40 base single strand synthetic fragments of the C. trachomatis and C. pneumoniae.groEL gene which encodes heat shock protein 60 (HSP60).
2. A single padlock probe was used that annealed to conserved sequences, leaving a gap that included species specific sequence.
3. The primers were designed as follows. Primer FVCOMT is antisense with respect to the padlock probe and is designed to anneal to the padlock backbone ie., the part of the padlock probe that does not anneal to the target. It also contains an oligosaccharide-T domain at its 5' end to act as a spacer between it and the solid support. The allele specific primers are in the same sense as the padlock probe and spacer sequence and are designed such that the 4 bases at the 3' end are the same as the 4 bases at the 5' end of the spacer sequences.
4. The annealing/ligation reaction was carried out in the presence of target, padlock and both allele specific spacers.
5. The circles were then interrogated in a solid phase amplification (SPA) RCA reaction using allele specific primers. Amplification only took place when the primer included in the reaction matched the spacer that was incorporated into the circle as dictated by the target sequence.

Ligation

The ligation consisted of 1×T4 DNA ligase buffer (Life Technologies), 6 pmoles padlock HSP2, 52 pmoles Pne spacer, 52 pmoles Tra spacer, 3.2 U T4 DNA ligase (Life Technologies) and 50 pmoles synthetic target in a 40 µL reaction. Ligations were performed at room temperature for 20 minutes after a 3 minute denaturation at 94° C.

RCA

Nunc wells with FVComT covalently bound, were blocked with 50 µL 10 mg/mL BSA for 1 hour. The reactions contained 1×thermopolymerase buffer (New England BioLabs), 10 mM dNTP's (Boehringer Mannheim), 10 pmoles FVComT, 10 pmoles of labelled Pne 4 or Tra 4, 4 U BST DNA polymerase large fragment (New England BioLabs) and 1 µL ligated circles in a 60 µL reaction. After an initial denaturation of 94° C. for 3 minutes, isothermal RCA reactions were performed at 55° C. for 1 hour 40 minutes, on a MJ Research, Peltier Thermal Cycler-200.

Solid Phase Detection

RCA Solution was removed from wells by washing 3× with TBST at room temperature (100 mM TRIS-HCl pH 7.5, 150 mM NaCl, and 0.1% v/v Tween 20). Wells were blocked with 50 µL 10 mg/mL BSA for 30 minutes and washed 3× with TBST. Anti-Fluorescein alkaline phosphatase antibody, (Boehringer Mannheim) diluted 1:3000 in TBST, was added to wells (50 µL) for 30 minutes. Wells were washed 6× with TBST and 2× with TBS (100 mM TRIS-HCl pH 7.5, 150 mM NaCl). To each well, 50 µL PNPP (Sara nitrophenylene phosphate) substrate (Sigma) (1 mg/mL made up in 0.2M Tris) was added, under dark conditions. Wells were read at 405 nm after the indicated times.

Covalent Binding of FVCOMT to Nunc Wells

The coating mix contained 100 nM FVComT, 10 mM EDC (1-ethyl-3-(3-dimethylaminopropyl)-carbodiimide) and 10 mM 1-methyl-imidiazole. To each well 100 µL was added and the wells were sealed and incubated at 50° C. overnight. Wells were washed 3×TBST, then soaked for 5 minutes and washed with 3×TBST. To remove residual salt, wells were washed once with deionised water and stored at 4° C.

Oligonucleotide Sequences

C. pneumoniae derived synthetic target:

TCCTTAACTTTCTATAATCTGCAAACTAGTATTTTATTTTAGGACGGCCA
TG <400>27

C. trachomatis derived synthetic target:

TCCTTAAATCTTCTTCACTCTCTTAGTTTTTATTGCAGAACTGCGATA
<400>28

C. pneumoniae specific spacer (SPACER PNE): 5'6AA GbT AAC3'

C. trachomatis specific spacer (SPACER TRA): 5'6bT GCA AAC3'

Padlock probe (LOCKHSP2): 5'6GC AGG TAA AGA AGG CGCC CGC GGT GAG CTA TAT GGG GAC TAT GAA TTT GCT CCA TTA AAG CAA ATT GC3' <400>30

C. pneumoniae specific primer (PNE4): 5'7CC ATT AAA GCA AAT TGC AAG T3' <400>30

C. trachomatis specific primer (TRA4): 5'7CC ATT AAA GCA AAT TGC TGC A3' <400>31

6=PHOSPHATE

7=FAM b=BIOTIN

Results (i) Colourmetric Detection of Immobilised Allele-Specific Primers ie., SPA Reactions The readings are absorbances at 405 nanometers and the results are depicted in Table 1. It can be seen that in all cases the highest readings were obtained with matching target/primer sequences.

(ii) Solution Phase Material, Demonstrating Concordance with Spa Readings and Amplification.

Figure 20:
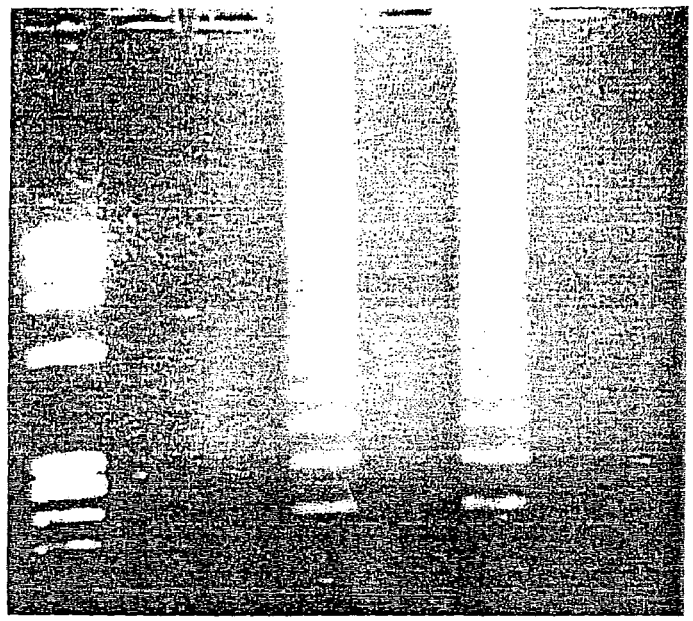
FIG. 20 is a photographic representation of the solution phase material produced in the reaction described in Example 11.

Results are depicted in FIG. 20.

EXAMPLE 12

Solid Phase Amplification (SPA) and Detection of the Factor V Leiden Mutation

Padlock Circularisation

Utilizing the closed circular probe generation (tagged spacer) and purification protocols the ability of rolling circle amplification to initiate from primers immobilized on solid supports was tested. Both positive and negative control ligations were setup. The negative (–ve) and positive (+ve) control reactions both contained 1 pmol of each Padlock FV2, Lig W and wildtype target oligonucleotides. Both reactions were heated to 94° C. and then 1 µL of Ampligase was added to the positive control reaction only. The reactions were cooled to 60° C. and incubated for 1 hour to allow ligation to take place. Following ligation both reactions were purified by the outlined protocol. Padlocks and oligonucleotide sequences are described in FIG. 4.

Solid Phase Amplification

FVComT primer (5 pmol) was covalently linked to Nucleolink plates (Nunc) according to the manufacturers instructions. The plates were blocked in 1% w/v BSA (100 mg/mL) in TBST buffer (100 mM Tris HCl pH 7.5; 150 mM NaCl; 0.05% v/v Tween-20) by incubated for 30 minutes at room temperature. The blocking solution was subsequently removed from the plates and amplification reactions assembled in the wells. Standard 60 µL reactions were setup each containing 10 pmol of fluorescently labelled FVW1 primer. Various amounts of additional FVComT primer were also added to the well for the positive control reactions but in solution rather than attached to the wells. A single reaction containing 10 pmol of FVW1 and 10 pmol of FVComT in addition to primer bound to the wells was used to test the negative control reaction. 1 µL of the respective templates was added to each reaction and the wells were heated at 94° C. for 3 minutes and then cooled to 60° C. Bst polymerase (4 units) was added and the wells were incubated for 100 minutes at 60° C.

Detection-Solution Phase

Following amplification, 10 µL of each of the RCA reactions was run on a 2% w/v agarose gel and stained with ethidium bromide to visualise the solution phase products of the RCA reaction.

Figure 21:
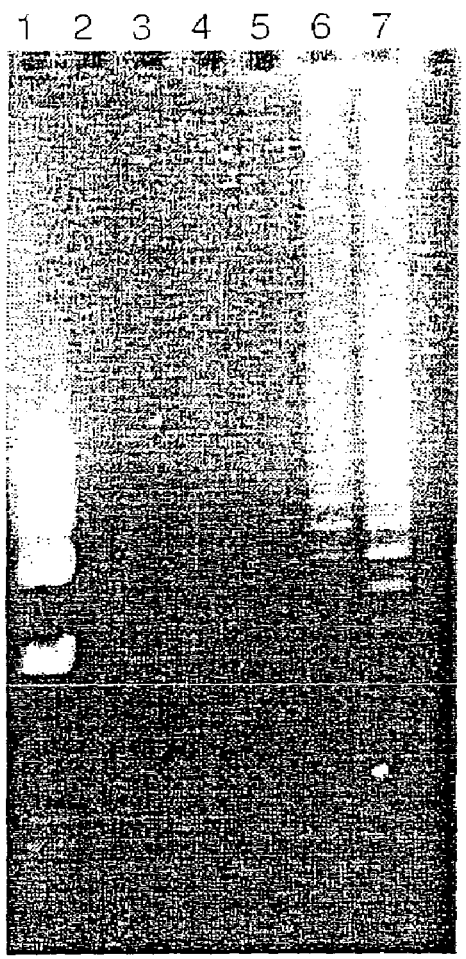
FIG. 21 is a photographic representation of solution phase material produced in the reaction described in Example 12.

As expected no products were visible for the negative control reaction. Products were visible in the solution phase for some of the positive control reactions. As anticipated the greatest amount of product was seen when 10 pmol of additional FVComT was added to the solution phase of the reactions (FIG. 21). As the level of additional solution phase FVComT was reduced so too was the amount of product visualized. No products were visible, however, when 0.1 pmol or less of FVComT primer was added (FIG. 21).

Solid Phase Detection

Following amplification the wells were washed three times in TBST (20 mM Tris HCl pH 7.5, 150 mM NaCl, 0.05% v/v Tween) and blocked with 1% w/v BSA in TBST by incubating at room temperature for 30 minutes. The wells were then washed 3 times in TBST. 50 µL of anti-fluorescein alkaline phosphatase conjugate antibody, diluted 1 in 5000 with TBST was added to each well and incubated at room temperature for 30 minutes. The wells were then washed 6 times in TBST and 2 times in TBS (20 mM Tris HCl pH 7.5, 150 mM NaCl). 50 µL of pNPP alkaline phosphatase substrate (SIGMA) was added to each well and the plates were kept in the dark for 40 minutes. The plate were then read at 405 nm. The results are depicted in Table 2.

Strong absorbance readings were obtained after 40 minutes. All positive control reactions were at least 3 fold higher than the negative control. Changing the concentration of the additional solution phase FVComT primer did not appear to dramatically alter the level of signal produced.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

|  | −ve 1 | −ve 2 | Pne+ | Pne− | Tra+ | Tra− | Blank |
| --- | --- | --- | --- | --- | --- | --- | --- |
| ½ hour | 0.228 | 0.118 | 0.519 | 0.122 | 0.466 | 0.168 | 0.057 |
| 1 hour | 0.386 | 0.181 | 0.983 | 0.183 | 0.848 | 0.262 | 0.141 |
| 2 hours | 0.703 | 0.316 | 1.878 | 0.312 | 1.634 | 0.482 | 0.049 |

−ve 1: No target, *C. pneumoniae* specific primer
−ve 2: *C. pneumoniae* target, *C. pneumoniae* specific primer, no ligase
Pne+: *C. pneumoniae* target, *C. pneumoniae* specific primer
Pne−: *C. pneumoniae* target, *C. trachomatis* specific primer
Tra+: *C. trachomatis* target, *C. trachomatis* specific primer
Tra−: *C. trachomatis* target, *C. pneumoniae* specific primer
Blank: colour development reagents only.

TABLE 2

|  | No target, 10 pmoles FVComT | 0 pmoles Fcvomt | 0.1 pmoles Fvcomt | 1 pmoles Fvcomt | 5 pmoles Fvcomt | 10 pmoles Fvcomt | No target, padlock or spacer |
| --- | --- | --- | --- | --- | --- | --- | --- |
| 40 min | 0.154 | 0.771 | 0.602 | 0.859 | 0.606 | 0.575 | 0.044 |
| 90 min | 0.317 | 1.829 | 1.748 | 2.083 | 1.499 | 1.361 | 0.046 |
| 120 min | 0.450 | 2.653 | 2.511 | 2.904 | 2.162 | 1.998 | 0.049 |

BIBLIOGRAPHY

1. Saiki, R. K., Scharf, S., Faloona, F., Mullis, K. B., Horn, G. T., Erlich, H. A. & Arnheim, N. (1985). *Science* 230:1350-1354.
2. Landegren, U., Kaiser, R., Sanders, J. & Hood, L. (1988). *Science* 241:1077-1080.
3. Kwoh, D. Y., Davis, G. R., Whitfield, K. M., Chappelle, H. L., DiMichele, L. J. & Gingeras, T. R. (1989). *Proceedings of the National Academy of Sciences, USA* 86: 1173-1177.
4. Lizardi, P. M., Guerra, C. E., Lomeli, H., Tussie-Luna, I. & Kramer, F. R. (1988). *Bio/technology* 6:1197-1202.
5. Guatelli, J. C., Whitfield, K. M., Kwoh, D. Y., Barringer, K. J., Richman, D. D. & Gingeras, T. R. (1990). *Proceedings of the National Academy of Sciences, USA* 87: 1874-1878.
6. Kievitis, T., vanGemen, G., vanStrijp, D., Schukkink, R., Dircks, M., Adriaanse, H., Malek, L., Sooknanan, R. & Lens, P. (1991). *Journal of Virological Methods* 35:273-286.
7. Walker, G. T., Fraiser, M. S., Schram, J. L., Little, M. C., Nadeau, J. G. & Malinowski, D. P. (1992). *Nucleic Acids Research* 20:1691-1696.
8. Lizardi, P. M., Huang, X., Zhu, Z., Bray-Ward, P., Thomas, D. C. & Ward, D. C. (1998) *Nature Genetics* 19:225-32.
9. Zhang, D. Y., Brandwein, M., Hsuih, T. C. & Li, H. (1998) *Gene* 211:277-85.

10. Kleckner, N., Bender, J. & Gottesman, S. (1991) *Methods in Enzymology* 204:139-180.
11. Silhavy, T. J., Berman, M. L. & Enquist, L. W. (1984) Cold Spring Harbor Laboratory Press, Cold Spring Harbor, N.Y.
12. Sambrook, J., Frisch, E. F., Maniatis, T. (1989) Molecular Cloning: a laboratory manual, 2nd ed. Cold Spring Harbor Laboratory Press, Cold Spring Harbor, N.Y.
13. Dower, W. J., Miller, J. F. & Ragsdale, C. W. (1988) *Nucleic Acids Research* 16:6127-6145.

What is claimed is:

1. A method for forming a circular nucleic acid probe comprising contacting a first target nucleic acid sequence molecule and a second target nucleic acid sequence molecule with a first nucleic acid probe and a second nucleic acid probe, wherein the nucleic acid probes each comprise a 5' target probe region and a 3' target probe region, wherein the 5' target probe region of the first nucleic acid probe hybridizes to the first target nucleic acid sequence molecule, wherein the 3' target probe region of the first nucleic acid probe hybridizes to the second target nucleic acid sequence molecule, wherein the 3' target probe region of the second nucleic acid probe hybridizes to the first target nucleic acid sequence molecule, wherein the 5' target probe region of the second nucleic acid probe hybridizes to the second target nucleic acid sequence molecule, wherein the target nucleic acid sequences of the first and second target nucleic acid sequence molecules are different, circularizing the first and second nucleic acid probes thereby forming a circular nucleic acid probe, wherein the gap between the 5' end of the first nucleic acid probe and the 3' end of the second nucleic acid probe is closed and wherein the gap between the 3' end of the first nucleic acid probe and the 5' end of the second nucleic acid probe is closed.

2. The method of claim 1 further comprising, subjecting the circular nucleic acid probe to rolling circle amplification, wherein the rolling circle amplification uses one or more complementary primers, wherein the complementary primers are complementary to the nucleic acid probe, wherein the rolling circle amplification uses one or more sense primers, wherein the rolling circle amplification produces a nucleic acid strand complementary to the nucleic acid probe, wherein the sense primers are complementary to the nucleic acid strand complementary to the nucleic acid probe, wherein the sense primers interact with regions of the nucleic acid strand complementary to the nucleic acid probe.

3. The method of claim 2 conducted in solid phase.

4. The method of claim 1 further comprising subjecting the circular nucleic acid probe to amplification.

5. The method of claim 4 wherein said amplification is rolling circle amplification.

6. The method of claim 5 wherein said rolling circle amplification is multiple primer rolling circle amplification.

* * * * *